(12) United States Patent
Orkin et al.

(10) Patent No.: US 10,266,826 B2
(45) Date of Patent: *Apr. 23, 2019

(54) MODULATION OF BCL11A FOR TREATMENT OF HEMOGLOBINOPATHIES

(71) Applicants: THE CHILDREN'S MEDICAL CENTER CORPORATION, Boston, MA (US); PRESIDENT AND FELLOWS OF HARVARD COLLEGE, Cambridge, MA (US)

(72) Inventors: Stuart H. Orkin, Brookline, MA (US); Vijay G. Sankaran, Jamaica Plain, MA (US)

(73) Assignees: Children's Medical Center Corporation, Boston, MA (US); President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/888,350

(22) Filed: Feb. 5, 2018

(65) Prior Publication Data

US 2018/0179527 A1   Jun. 28, 2018

Related U.S. Application Data

(63) Continuation of application No. 14/987,219, filed on Jan. 4, 2016, now Pat. No. 9,885,041, which is a continuation of application No. 13/743,399, filed on Jan. 17, 2013, now Pat. No. 9,228,185, which is a continuation of application No. 13/063,524, filed as application No. PCT/US2009/056770 on Sep. 14, 2009, now Pat. No. 8,383,604.

(60) Provisional application No. 61/097,017, filed on Sep. 15, 2008, provisional application No. 61/222,571, filed on Jul. 2, 2009.

(51) Int. Cl.

| C07H 21/02 | (2006.01) |
| C07H 21/04 | (2006.01) |
| A61K 31/70 | (2006.01) |
| C12N 15/113 | (2010.01) |
| A61K 49/00 | (2006.01) |
| A61K 35/28 | (2015.01) |
| C12N 5/0789 | (2010.01) |
| C12N 15/86 | (2006.01) |
| C12N 15/85 | (2006.01) |
| C07K 14/805 | (2006.01) |
| C07K 14/47 | (2006.01) |
| A01K 67/027 | (2006.01) |
| A61K 31/713 | (2006.01) |
| C12Q 1/00 | (2006.01) |
| C12N 5/00 | (2006.01) |

(52) U.S. Cl.
CPC ........ *C12N 15/113* (2013.01); *A01K 67/0275* (2013.01); *A61K 31/713* (2013.01); *A61K 35/28* (2013.01); *A61K 49/00* (2013.01); *C07K 14/4705* (2013.01); *C07K 14/805* (2013.01); *C12N 5/0647* (2013.01); *C12N 15/8509* (2013.01); *C12N 15/86* (2013.01); *C12Q 1/00* (2013.01); *A01K 2217/052* (2013.01); *A01K 2217/15* (2013.01); *A01K 2227/105* (2013.01); *A01K 2267/0381* (2013.01); *C12N 2310/14* (2013.01); *C12N 2310/531* (2013.01); *C12N 2740/15043* (2013.01); *C12N 2800/206* (2013.01)

(58) Field of Classification Search
None
See application file for complete search history.

(56) References Cited

U.S. PATENT DOCUMENTS

| 5,928,638 A | 7/1999 | Uchida et al. |
| 9,228,185 B2 | 1/2016 | Orkin et al. |
| 9,885,041 B2 | 2/2018 | Orkin et al. |
| 2004/0259247 A1 | 12/2004 | Tuschl et al. |
| 2005/0227917 A1 | 10/2005 | Williams et al. |
| 2008/0051431 A1 | 2/2008 | Verhelle et al. |
| 2010/0273213 A1 | 10/2010 | Mineno et al. |

FOREIGN PATENT DOCUMENTS

| EP | 1752536 A1 | 2/2007 |
| EP | 2334794 B1 | 11/2016 |
| EP | 2334794 B8 | 4/2017 |
| JP | 2006507841 A | 3/2006 |
| WO | 2009/007685 A2 | 1/2009 |
| WO | 2010/030963 A2 | 3/2010 |
| WO | 2015/065964 A1 | 5/2015 |
| WO | 2016/182893 A1 | 11/2016 |

OTHER PUBLICATIONS

Bauer et al., "Supplementary Material: An Erythroid Enhancer of BCL11A Subject to Genetic Variation Determines Fetal Hemoglobin Level." Science 342(6155):253-257 (2013).
Bjurström et al. "Reactivating fetal hemoglobin expression in human adult erythroblasts through BCL11A knockdown using targeted endonucleases." Molecular Therapy-Nucleic Acids 5:e351 (2016).
Doench et al., "Rational design of highly active sgRNAs for CRISPR-Cas9-mediated gene inactivation." Nature Biotechnology 32(12):1262-1267 (2014).
Doench et al., "Supplementary Material: Rational design of highly active sgRNAs for CRISPR-Cas9-mediated gene inactivation." Nature Biotechnology 32(12):1262-1267 (2014).

(Continued)

*Primary Examiner* — Sean McGarry
(74) *Attorney, Agent, or Firm* — Nixon Peabody LLP

(57) ABSTRACT

The invention relates to methods and uses of modulating fetal hemoglobin expression (HbF) in a hematopoietic progenitor cells via inhibitors of BCL11A expression or activity, such as RNAi and antibodies.

32 Claims, 18 Drawing Sheets

Specification includes a Sequence Listing.

(56) References Cited

OTHER PUBLICATIONS

Sebastiani et al., "BCL11A enhancer haplotypes and fetal hemoglobin in sickle cell anemia." Blood Cells, Molecules, and Diseases 54(3):224-230 (2015).
Wang et al. "Genetic screens in human cells using the CRISPR/Cas9 system." Science 343(6166):80-84 (2013).
Wang et al. "Supplementary Material: Genetic screens in human cells using the CRISPR/Cas9 system." Science 343 (6166):80-84 (2013).
Atweh et al., Seminars in Hematology, 38(4):367-73 (2001). "Pharmacological induction of fetal hemoglobin in sickle cell disease and beta-thalassemia."
Bohmer et al., Prenatal Diagnosis, 19:628-636 (1999). "Identification of fetal nucleated red cells in co-cultures from fetal and adult peripheral blood: differential effects of serum on fetal and adult erythropoiesis."
Bunn et al., New Engl. J. Med., 328(2):129-131 (1993). "Reversing ontogeny."
Chabchoub et al., "The facial dysmorphy in the newly recognised microdeletion 2p15-p16.1 refined to a 570 kb region in 2p15", J Med Genet, 45(3):189-92 (2008).
Coleman et al., Clinical Pediatrics, 46(5):386-391 (2007). "Sickle cell anemia: targeting the role of fetal hemoglobin in therapy."
Dixit et al., Ann Hematol, 84:441-446 (2005).
Fenaux, "Inhibitors of DNA methylation: beyond myelodysplastic syndromes", Nat Clin Pract Oncol., 2:S36-S44 (2005).
Fischer et al., "Pulmonary Passage is a Major Obstacle for Intravenous Stem Cell Delivery: The Pulmonary First-Pass Effect", Stem Cells and Development, 18(5):683-91 (2009).
Flanagan et al., British Journal of Haematology, 157:240-248 (2012).
GeneCard for BCL11A, retrieved from http://www.genecards.org/cgi-bin/carddisp.pl?gene=BCL11A on Jun. 22, 2012.
Goffin et al., "DNA methyltransferase inhibitors-state of the art", Ann Oncol.,13(11):1699-716 (2002).doi: 10.1093/annonc/mdf314.
Goldberg et al., N Engl J Med, 323:366-372 (1990).
Hackam "Translating animal research into clinical benefit", BMJ, 334:163-68 (2007).
Higgs et al., Proceedings of the National Academy of Sciences, 105(33):11595-11596 (2008). "Genetic complexity in sickle cell disease."
Ho et al., Exp Hematol, 31:586-591 (2003).
Hsieh et al., "Allogeneic hematopoietic stem-cell transplantation for sickle cell disease", N Engl J Med, 361 (24):2309-17 (2009).
Jane et al., Br. J. Haematol., 102:415-422 (1998). "Understanding fetal globin gene expression: a step towards effective HbF reactivation in haemoglobinopathies."
Kauf et al., "The cost of health care for children and adults with sickle cell disease", Am J Hematol, 84(6):323-7 (2009).
Kirschner et al., "Genomic mapping of chromosomal region 2p15-p21 (D2S378-D2S391): integration of Genemap'98 within a framework of yeast and bacterial artificial chromosomes", Genomics, 62(1):21-33 (1999).
Koshy et al., "2-deoxy 5-azacytidine and fetal hemoglobin induction in sickle cell anemia", Blood, 96(7):2379-84 (2000).
Labie, Hematologie, 14(2):165-166 (2008). "Le controle en trans de la production dEhemoglobine flltale: une recherche qui dure deupis 20 ans."
Lettre, G. et al., PNAS, 105(33):11869-11874 (2008). "DNA polymorphisms at the BCL11A, HBS1L-MYB, and beta-globin loci associate with fetal hemoglobin levels and pain crises in sickle cell disease."
Liu et al., Nature Immun, 4:525-532 (2003). "Bcl11a is essential for normal lymphoid development." ((from Prov)).
Martin-Subero et al., Blood, 99:1474-1477 (2002). "Recurrent involvement of the REL and BCL11A loci in classical Hodgkin lymphoma." ((from Prov)).
Menzel et al., Nature Genetics, 39(10):1197-1199 (2007). "A QTL influencing F cell production maps to a gene encoding a zinc-finger protein on chromosome 2p15."

Migliaccio et al., Blood 76(6):1150-1157 (1990). "Influence of recombinant hematopoietins and of fetal bovine serum on the globin synthetic pattern of human BFUe."
Moffat et al., "A lentiviral RNAi library for human and mouse genes applied to an arrayed viral high-content screen." Cell 124(6):1283-1298 (2006).
Papayannopoulou et al., Science, 199:1349-1350 (1978). "Erythroid progenitors circulating in the blood of adult individuals produce fetal hemoglobin in culture."
Pauling et al. "Sickle cell anemia a molecular disease", Science, 110(2865):543-8 (1949).
Pembrey et al., Br. J. Haematol., 40: 415-429 (1978). "Fetal haemoglobin production and the sickle gene in the bases of Eastern Saudi Arabia."
Perrine, "Fetal globin induction—can it cure beta thalassemia?", Hematology Am Soc Hematol Educ Program, pp. 38-44 (2005).
Platt et al., "Mortality in sickle cell disease. Life expectancy and risk factors for early death", N Engl J Med, 330 (23):1639-44 (1994).
Purton et al., Blood, 95(2):470-478 (2000).
Ridley et al., "Erythropoietin: A Review", J Natl Med Assoc., 86(2):129-35 (1994).
Rodriguez et al., Blood, 9(5):1533-1541 (1998).
Rosenblum et al., Experimental Approaches for the Study of Hemoglobin, 397 (1985). "Peripheral blood erythroid progenitors from patients with sickle cell anemia: HPLC separation of hemoglobins and the effect of a HbF switching factor."
Saiki et al., Genomics, 70:387-391 (2000).
Sankaran et al., Nature, 460(7259):1093-7 (2009). "Developmental and species-divergent globin switching are driven by BCL11A." ((from Prov)).
Sankaran, V.G., Science, 322:1839-1842 (2008). "Human fetal hemoglobin expression is regulated by the developmental stage-specific repressor BCL11A."
Satterwhite et al., Blood, 98:3413-3420 (2001). "The BCL11 gene family: involvement of BCL11A in lymphoid malignancies." ((from Prov)).
Sedgewick, A.E., Blood Cells, Molecules and Diseases, 41:255-258 (2008). "BCL11A is a major HbF quantitative trait locus in three different populations with beta-hemoglobinopathies."
Shen et al., Experimental Hematology, 35(8):1209-1218 (2007). "Modifcation of globin gene expression by RNA targeting strategies."
Taymans et al., "Radiation hybrid mapping of chromosomal region 2p15-p16: integration of expressed and polymorphic sequences maps at the Carney complex (CNC) and Doyne honeycomb retinal dystrophy (DHRD) loci", Genomics, 56:344-9 (1999).
Thein, British Journal of Haematology, 145:455-467 (2009). "Discovering the genetics underlying foetal haemoglobin production in adults."
Thein, S.L., British Journal of Hematology, 141:357-366 (2008). "Genetic modifiers of the beta-haemoglobinopathies." ((from Prov)).
Thompson, "Structure, Function, and Molecular Defects of Factor IX", Blood, 67(3):565-72 (1986).
Uda, M. et al., PNAS, 105(5):1620-1625 (2008). "Genome-wide association study shows BCL11A associated with persistent fetal hemoglobin and amelioration of the phenotype of beta-thalassemia."
White et al., "Factor VIII Gene and Hemophililia A", Blood, 73(1):1-12 (1989).
World Health Organization. "Sickle-cell anaemia. Report A59/9. Provisional agenda item 11.4." 59th World Health Assembly. www.who.int/gb/ebwha/pdf_files/WHA59/A59_9-en.pdf (2006).
Yin et al., "Bcl11a Causes p21 Cip1 Down-Regulation and Transplantable Leukemia in Nf1-Deficient Mice." Blood 110 (11):2657-2657 (2007) [Abstract Only].
Examination Search Report dated May 11, 2018 in corresponding Canadian Application CA 2737180.
Wang et al., "Selection of hyperfunctional siRNAs with improved potency and specificity." Nucleic Acids Research 37(22):e152 (2009).
Bauer et al., "HbF-Associated Genetic Variation Marks an Erythroid Regulatory Element Essential for BCL11A Transcription and Subsequent Stage-Specific Globin Expression." Blood 120:828 (2012).

(56) References Cited

OTHER PUBLICATIONS

Hancarova et al. "A patient with de novo 0.45 Mb deletion of 2p16.1: The role of BCL11A, PAPOLG, REL, and FLJ16341 in the 2p15-p16.1 microdeletion syndrome." American Journal of Medical Genetics Part A 161(4):865-870 (2013).

Hendel et al., "Chemically modified guide RNAs enhance CRISPR-Cas genome editing in human primary cells." Nature Biotechnology 33(9):985-989 (2015).

Liu et al., "Functional studies of BCL11A: characterization of the conserved BCL11A-XL splice variant and its interaction with BCL6 in nuclear paraspeckles of germinal center B cells." Molecular Cancer 5(18):1-6 (2006).

Figure 3A
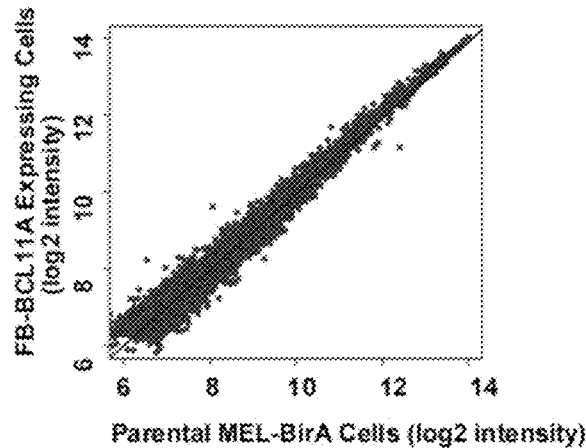
Figure 3B
| Protein | Peptides |
|---|---|
| BCL11A | 29,49 |
| GATA-1 | 1,1 |
| CHD4 | 16,10 |
| RBBP4 | 8,15 |
| MT A2 | 6,18 |
| p66b | 5,16 |
| MT A1 | 9,12 |
| p66a | 3,8 |
| HDAC1 | 11,11 |
| HDAC2 | 4,3 |
| RBBP7 | 4,5 |
| MT A3 | 1,1 |
| MBD3 | 5,3 |
| MATRIN-3 | 8,9 |
Figure 3C
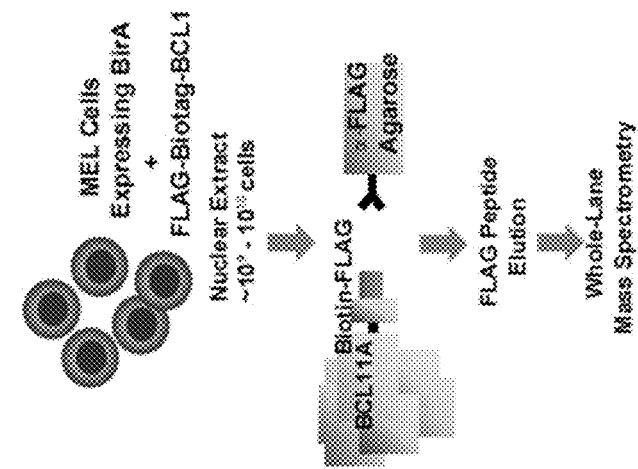
Figure 3D
| | | |
|---|---|---|
| mBCL11A | MSRRKQGKPQHLSKRE | (SEQ.ID. No. 22) |
| hsBCL11A | MSRRKQGKPQHLSKRE | (SEQ.ID. No. 23) |
| mBCL11B | MSRRKQGNPQHLSQRE | (SEQ.ID. No. 24) |
| mFOG-1 | MSRRKQSNPQIKRSL | (SEQ.ID. No. 25) |
| mEvi3 | MSRRKQAKPRSLKDPN | (SEQ.ID. No. 26) |
| mEBFA2 | MSRRKQAKPRSVRVEE | (SEQ.ID. No. 27) |
| mSALL1 | MSRRKQAKPQHFQSDP | (SEQ.ID. No. 28) |

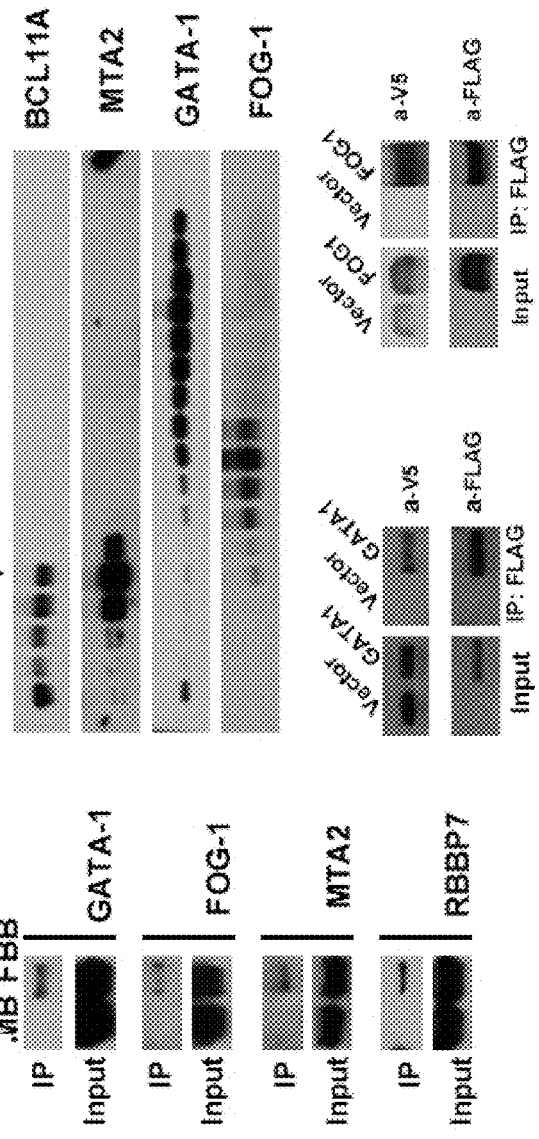

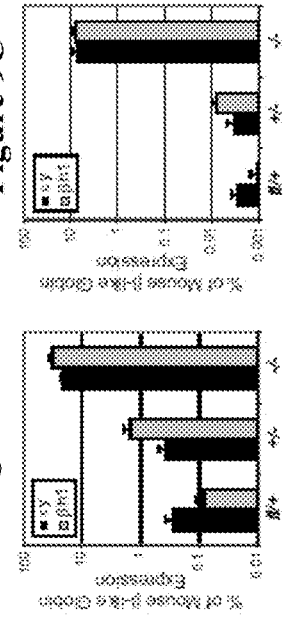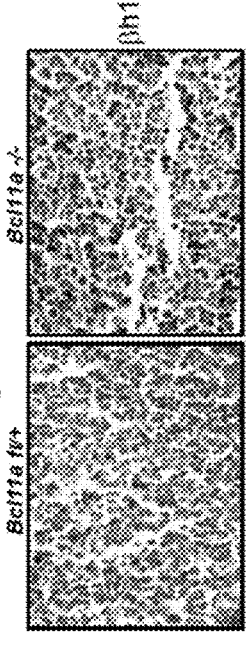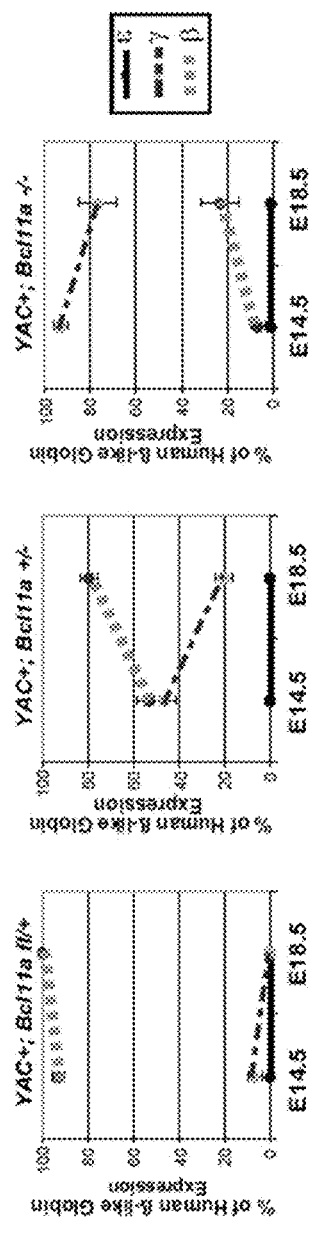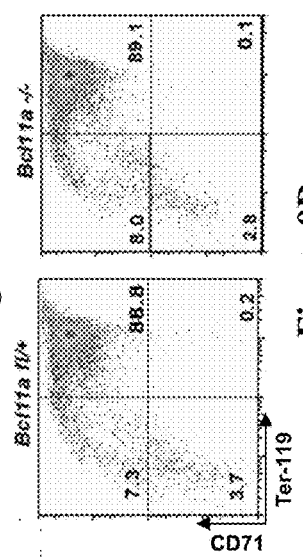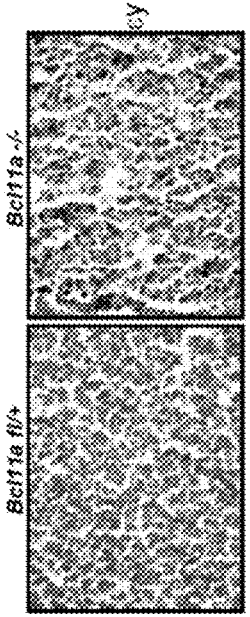

Figure 18A

| E14.5 Fetal Liver | | YAC+; Bcl11a fl/+ (n=4) | YAC+; Bcl11a +/- (n=6) | YAC+; Bcl11a -/- (n=4) |
|---|---|---|---|---|
| % of Human β-like Globin Expression | ε | 0.022 ± 0.011 | 0.043 ± 0.026 | 0.37 ± 0.14 |
| | γ | 6.75 ± 2.84 | 46.39 ± 5.18 | 93.33 ± 2.91 |
| | β | 93.22 ± 2.83 | 53.56 ± 5.17 | 6.30 ± 3.03 |

Figure 18B

| E18.5 Fetal Liver | | YAC+; Bcl11a fl/+ (n=4) | YAC+; Bcl11a +/- (n=7) | YAC+; Bcl11a -/- (n=4) |
|---|---|---|---|---|
| % of Human β-like Globin Expression | ε | 0.003 ± 0.001 | 0.012 ± 0.005 | 0.35 ± 0.08 |
| | γ | 0.24 ± 0.05 | 20.36 ± 3.84 | 76.65 ± 8.35 |
| | β | 99.76 ± 0.05 | 79.63 ± 3.84 | 23.00 ± 8.36 |

MODULATION OF BCL11A FOR TREATMENT OF HEMOGLOBINOPATHIES

CROSS REFERENCE TO RELATED APPLICATIONS

This application is a continuation application of U.S. patent application Ser. No. 14/987,219 filed on Jan. 4, 2016, issued as U.S. Pat. No. 9,885,041 on Feb. 6, 2018, which is a continuation application of U.S. patent application Ser. No. 13/743,399 filed on Jan. 17, 2013, issued as U.S. Pat. No. 9,228,185 on Jan. 5, 2016, which is a continuation application of U.S. patent application Ser. No. 13/063,524 filed on Apr. 14, 2011, issued as U.S. Pat. No. 8,383,604 on Feb. 26, 2013 and is a 35 U.S.C. § 371 National Phase Entry Application of International Application No. PCT/US2009/056770 filed Sep. 14, 2009, which designates the U.S., and which claims benefit under 35 U. S. C. § 119(e) of U.S. Provisional Application No. 61/097,017 filed on Sep. 15, 2008 and U.S. Provisional Application No. 61/222,571 filed on Jul. 2, 2009, the contents of each are incorporated herein by reference in their entireties.

GOVERNMENT SUPPORT

This invention was made with Government Support under T32 GM07726, T32 GM07753-27, 5P01 HL32262-26, and 5R01 HL32259-27, all awarded by the National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Jan. 4, 2016, is named 20160104_SequenceListing-TextFile_701039_069896_C.txt and is 6,427 bytes in size.

BACKGROUND OF THE INVENTION

Normal adult hemoglobin comprises four globin proteins, two of which are alpha ($\alpha$) proteins and two of which are beta ($\beta$) proteins. During mammalian fetal development, particularly in humans, the fetus produces fetal hemoglobin, which comprises two gamma ($\gamma$)-globin proteins instead of the two $\beta$-globin proteins. At some point during fetal development or infancy, depending on the particular species and individual, a globin switch occurs, referred to as the "fetal switch", at which point, erythrocytes in the fetus switch from making predominantly $\gamma$-globin to making predominantly $\beta$-globin. The developmental switch from production of predominantly fetal hemoglobin or HbF ($\alpha_2\gamma_2$) to production of adult hemoglobin or HbA ($\alpha_2\beta_2$) begins at about 28 to 34 weeks of gestation and continues shortly after birth until HbA becomes predominant. This switch results primarily from decreased transcription of the gamma-globin genes and increased transcription of beta-globin genes. On average, the blood of a normal adult contains only about 2% HbF, though residual HbF levels have a variance of over 20 fold in healthy adults (Atweh, Semin. Hematol. 38(4):367-73 (2001)).

Hemoglobinopathies encompass a number of anemias of genetic origin in which there is a decreased production and/or increased destruction (hemolysis) of red blood cells (RBCs). These also include genetic defects that result in the production of abnormal hemoglobins with a concomitant impaired ability to maintain oxygen concentration. Some such disorders involve the failure to produce normal $\beta$-globin in sufficient amounts, while others involve the failure to produce normal $\beta$-globin entirely. These disorders associated with the $\beta$-globin protein are referred to generally as $\beta$-hemoglobinopathies. For example, $\beta$-thalassemias result from a partial or complete defect in the expression of the $\beta$-globin gene, leading to deficient or absent HbA. Sickle cell anemia results from a point mutation in the $\beta$-globin structural gene, leading to the production of an abnormal (sickled) hemoglobin (HbS). HbS RBCs are more fragile than normal RBCs and undergo hemolysis more readily, leading eventually to anemia (Atweh, Semin. Hematol. 38(4):367-73 (2001)).

Recently, the search for treatment aimed at reduction of globin chain imbalance in patients with $\beta$-hemoglobinopathies has focused on the pharmacologic manipulation of fetal hemoglobin ($\alpha2\gamma2$; HbF). The therapeutic potential of such approaches is suggested by observations of the mild phenotype of individuals with co-inheritance of both homozygous $\beta$-thalassemia and hereditary persistence of fetal hemoglobin (HPFH), as well as by those patients with homozygous $\beta°$-thalassemia who synthesize no adult hemoglobin, but in whom a reduced requirement for transfusions is observed in the presence of increased concentrations of fetal hemoglobin. Furthermore, it has been observed that certain populations of adult patients with $\beta$ chain abnormalities have higher than normal levels of fetal hemoglobin (HbF), and have been observed to have a milder clinical course of disease than patients with normal adult levels of HbF. For example, a group of Saudi Arabian sickle-cell anemia patients who express 20-30% HbF have only mild clinical manifestations of the disease (Pembrey, et al., Br. J. Haematol. 40: 415-429 (1978)). It is now accepted that hemoglobin disorders, such as sickle cell anemia and the $\beta$-thalassemias, are ameliorated by increased HbF production. (Reviewed in Jane and Cunningham Br. J. Haematol. 102: 415-422 (1998) and Bunn, N. Engl. J. Med. 328: 129-131 (1993)).

As mentioned earlier, the switch from fetal hemoglobin to adult hemoglobin ($\alpha2\gamma2$; HbA) usually proceeds within six months after parturition. However, in the majority of patients with $\beta$-hemoglobinopathies, the upstream $\gamma$ globin genes are intact and fully functional, so that if these genes become reactivated, functional hemoglobin synthesis could be maintained during adulthood, and thus ameliorate disease severity (Atweh, Semin. Hematol. 38(4):367-73 (2001)). Unfortunately, the in vivo molecular mechanisms underlying the globin switch are not well understood.

Evidence supporting the feasibility of reactivation of fetal hemoglobin production comes from experiments in which it was shown that peripheral blood, containing clonogenic cells, when given the appropriate combination of growth factors, produce erythroid colonies and bursts in semisolid culture. Individual cells in such colonies can accumulate fetal hemoglobin (HbF), adult hemoglobin (HbA) or a combination of both. In cultures from adult blood, nucleated red cells accumulate either HbA (F−A+) only, or a combination of HbF and HbA (F+A+) (Papayannopoulou, et al., Science 199: 1349-1350 (1978); Migliaccio, et al., Blood 76: 1150-1157 (1990)). Importantly, individual colonies contain both F+ and F− cells, indicating that both types are progeny from the same circulating stem cells. Thus, during the early stages of development in culture, cells execute an option, through currently unknown mechanisms, whether or not to express HbF. The proportion of adult F+ cells developing in culture does not appear to be preprogrammed in vivo, but appears to depend on culture conditions: A shift into the combined HbF and HbA expression pathway can, for example, be achieved in vitro by high serum concentrations, due to the activity of an unidentified compound that can be absorbed on activated charcoal (Bohmer, et al., Prenatal Diagnosis 19: 628-636 (1999); Migliaccio, et al., Blood 76: 1150 (1990); Rosenblum, et al., in: Experimental Approaches for the Study of Hemoglobin 397 (1985)).

Overall, identification of molecules that play a role in the globin switch is important for the development of novel therapeutic strategies that interfere with adult hemoglobin and induce fetal hemoglobin synthesis. Such molecules would provide new targets for the development of therapeutic interventions for a variety of hemoglobinopathies in which reactivation of fetal hemoglobin synthesis would significantly ameliorate disease severity and morbidity.

SUMMARY OF THE INVENTION

The invention relates to methods and uses of modulating fetal hemoglobin expression (HbF) via BCL11A.

The invention is based, in part, upon identification of a function for the BCL11A protein, namely that the BCL11A protein acts as a stage specific regulator of fetal hemoglobin expression.

Accordingly, the invention provides a method for increasing fetal hemoglobin levels in a cell, comprising the steps of contacting a hematopoietic progenitor cell with an effective amount of a composition comprising an inhibitor of BCL11A, whereby fetal hemoglobin expression is increased in the hematopoietic progenitor cell, or its progeny, relative to the cell prior to contacting.

The hematopoietic progenitor cell is contacted ex vivo, in vitro, or in vivo. In a further embodiment, the hematopoietic progenitor cell being contacted is of the erythroid lineage.

In one embodiment, the composition inhibits BCL11A expression. In one embodiment, the inhibitor of BCL11A expression is selected from a small molecule and a nucleic acid. In a preferred embodiment, the inhibitor is a nucleic acid comprising a BCL11A specific RNA interference agent or a vector encoding a BCL11A specific RNA interference agent. In a preferred embodiment, the RNA interference agent comprises one or more of the nucleotide sequences of SEQ ID NO: 1-6.

In one embodiment, the composition inhibits BCL11A activity. In one embodiment, the inhibitor of BCL11A activity is selected from the group consisting of an antibody against BCL11A or an antigen-binding fragment thereof, a small molecule, and a nucleic acid. In a more preferred embodiment, the nucleic acid is a BCL11A specific RNA interference agent, a vector encoding a RNA interference agent, or an aptamer that binds BCL11A. In a preferred embodiment, the RNA interference agent comprises one or more of the nucleotide sequences of SEQ ID NO: 1-6.

Accordingly, the invention provides a method for increasing fetal hemoglobin levels in a mammal in need thereof, comprising the step of contacting a hematopoietic progenitor cell in the mammal with an effective amount of a composition comprising an inhibitor of BCL11A, whereby fetal hemoglobin expression is increased in the mammal, relative to expression prior to the contacting.

In one embodiment, the mammal has been diagnosed with a hemoglobinopathy. In a further embodiment, the hemoglobinopathy is a β-hemoglobinopathy. In another embodiment, the hemoglobinopathy is a sickle cell disease. The sickle cell disease can be sickle cell anemia, sickle-hemoglobin C disease (HbSC), sickle beta-plus-thalassaemia (HbS/β+) and sickle beta-zero-thalassaemia (HbS/β0). In another embodiment, the hemoglobinopathy is β-thalassemia.

In one embodiment, the hematopoietic progenitor cell is contacted with the composition ex vivo or in vitro, and the cell or its progeny is administered to the mammal. In a further embodiment, the hematopoietic progenitor cell being contacted is of the erythroid lineage.

In one embodiment, the hematopoietic progenitor cell is contacted with a composition comprising an inhibitor of BCL11A and a pharmaceutically acceptable carrier or diluent. In a further embodiment, the composition comprising a BCL11A inhibitor is administered by injection, infusion, instillation, or ingestion.

In one embodiment, the composition comprising a BCL11A inhibitor inhibits the expression of BCL11A. In another embodiment, the inhibitor of BCL11A expression is selected from a small molecule and a nucleic acid. In a preferred embodiment, the nucleic acid is a BCL11A specific RNA interference agent or a vector encoding a RNA interference agent, or an aptamer that binds BCL11A. In a preferred embodiment, the RNA interference agent comprises one or more of the nucleotide sequences of SEQ ID NO: 1-6.

In one embodiment, the composition comprising a BCL11A inhibitor inhibits the activity of BCL11A. In another embodiment, the inhibitor of BCL11A activity is selected from the group consisting of an antibody against BCL11A or an antigen-binding fragment thereof, a small molecule, and a nucleic acid. In a preferred embodiment, the nucleic acid inhibitor of BCL11A activity is a BCL11A specific RNA interference agent, a vector encoding a RNA interference agent, or an aptamer that binds BCL11A. In another embodiment, the RNA interference agent comprises one or more of the nucleotide sequences of SEQ ID NO: 1-6.

Accordingly, the invention provides a method for identifying a modulator of BCL11A activity or expression, the method comprising contacting a hematopoietic progenitor cell with a composition comprising a test compound, and measuring the level of fetal hemoglobin or fetal hemoglobin mRNA in the hematopoietic progenitor cell or its progeny, wherein an increase in fetal hemoglobin is indicative that the test compound is a candidate inhibitor of BCL11A activity or expression.

In one embodiment, the hematopoietic progenitor cell is contacted in vivo, ex vivo, or in vitro. In one embodiment, the cell is of human, non-human primate, or mammalian origin. In one embodiment, the test compound is a small molecule, antibody or nucleic acid. In a preferred embodiment, the composition causes an increase in fetal hemoglobin expression.

BRIEF DESCRIPTION OF DRAWINGS

FIG. 1A shows the major BCL11A isoforms present in nuclear extracts of human erythroid cells.

FIG. 1B compares the expression of BCL11A and fetal hemoglobin in erythroid cells at different stages of human ontogeny.

FIGS. 3A-3D depict the proteomic affinity screen methodology used to identify BCL11A partner proteins in erythroid cells.

FIG. 3A depicts the scheme used for affinity purification in mouse erythroleukemia (MEL) cells.

FIG. 3B tabulates the results of the subtractive screen.

FIG. 3C displays the results of the analyses of the Affymetrix arrays.

FIG. 3D highlights the motif found in BCL11A and several other proteins suggested to mediate interactions with the NuRD repressor complex.

FIGS. 4A-4E show confirmations of the BCL11A interactions with GATA-1, FOG-1, and the NuRD complex in erythroid cells.

FIG. 4A shows immunoprecipitation data that confirms the interactions of BCL11A with GATA-1, FOG-1, MTA2, and RBBP7 in erythroid (MEL) cells.

FIG. 4B depicts the interactions of BCL11A with MTA2, GATA-1, and FOG-1 using gel filtration fractions from erythroid nuclear extracts.

FIGS. 4C and 4D show immunoprecipitation data that confirm the interactions of BCL11A with GATA-1 and FOG-1 respectively by exogenous expression in Cos7 cells.

FIG. 4E shows immunoprecipitation data to maps the interaction of BCL11A on the GATA-1 molecule.

FIG. 5A demonstrates that siRNA-mediated knockdown of BCL11A results in elevations of γ-globin mRNA levels in human erythroid progenitor cells.

FIG. 5B depicts that global gene expression is not modified greatly in cells targeted with BCL11A siRNA.

FIG. 5C shows that lentiviral-mediated shRNA delivery to human erythroid progenitors results in a 60%-97% knockdown.

FIG. 5D depicts that the shRNA targeted cells are morphologically indistinguishable from control treated cells.

FIG. 5E shows the induction of γ-globin mRNA in cells in response to knockdown of BCL11A.

FIG. 6A is a representative FACS plot showing FSC (linear scale) versus SSC (log scale) for E13.5 embryonic blood. Gating is shown to allow for the enrichment of primitive and definitive lineages.

FIG. 6B is a histogram showing the relative expression of murine εγ globin gene, human embryonic ε gene, and human γ-globin genes in the primitive population (P), as compared with the definitive population (D). Results are shown as mean±standard deviation (n>3 per group). P=0.98 for a two-sided t-test comparing the relative enrichment of εγ with γ-globin.

FIGS. 6C-6H are representatives immunohistochemical staining with an anti-HbF antibody from human and murine E13.5 fetal livers. All images are taken with a 60× objective.

FIG. 6C shows human fetal livers contain numerous erythroblasts, which all stain positive for γ-globin expression.

FIGS. 6D and 6E show that murine fetal liver definitive erythroblasts do not show major γ-globin staining and only occasional cells with megaloblastic primitive morphology show staining (arrows).

FIGS. 6E and 6F show many megaloblastic primitive cells in the circulation having highly positive staining (arrowheads in FIG. 6E; arrows in FIG. 6F), while smaller definitive erythrocytes are negative (in FIG. 6F as smaller light grey circles).

FIGS. 6G and 6H show staining performed on the single copy YAC lines A20 and A858 showed similar staining patterns. Positive staining was determined in comparison with background staining from transgene negative littermate controls.

FIGS. 7A and 7B show the expression of γ-globin predominates within the two lines in the primitive populations seen circulating in primitive blood cells (PBC) from embryos E11.5 and E13.5. Minor expression is seen in the mature definitive populations from fetal liver (FL) at E13.5. Many of these cells may represent primitive cells found within the FL parenchyma.

FIGS. 7C and 7D show a parallel expression of mεγ and hγ for PBC at E13.5 and FL at E13.5, respectively. The graphs depict the percentage of active loci and are measured for ≥100 nuclei per probe set at each time point.

FIG. 8A shows that in human cells full-length proteins of BCL11A (XL/L isoforms) are reduced within cell populations that express high levels of γ-globin, including primitive and fetal liver cells.

FIG. 8B is a schematic model summarizes the ontogeny of β-like globin gene regulation in humans, mice, and β-locus mice. The ontogeny of mammalian erythropoiesis and progenitor populations is shown at the top. Progenitor populations, including primitive erythroid populations (EryP-CFC), definitive hematopoietic stem cells (HSC), and definitive erythroid burst-forming unit cells (BFU-E) are depicted. The aorto gonado-mesonephros (AGM) and placenta are sites of definitive hematopoiesis. The patterns of β-like globin and BCL11A expression seen in the two species are shown below.

FIGS. 9A-9F shows that BCL11A−/− mice fail to silence expression of mouse embryonic β-like globins and human β-globin genes.

FIG. 9A shows that he CD71/Ter119 expression pattern for fetal liver cells from E14.5 embryos, revealing grossly normal erythropoiesis with these phenotypic markers. The mean percentages for the populations in each quadrant are shown in red (n=6 for fl/+ controls and n=4 for −/− mutants). The P>0.1 by a two-sided t-test for all gated populations analyzed.

FIG. 9B shows that the expression of the embryonic globins as a percentage of total mouse β-like globins for control mice (fl/+), BCL11A heterozygous (+/−), and null mice (−/−) at E14.5 (n=10, 14, 11 respectively).

FIG. 9C shows that the expression of the embryonic globins as a percentage of total mouse β-like globins at E18.5 (n=9, 9, 7 respectively).

FIG. 9D shows the immunohistochemistry was performed on E14.5 FLs from BCL11A fl/+ and −/− animals for the embryonic globin εy. Representative sections at 40× magnification with a 10× objective lens are shown.

FIG. 9E shows similar IHC staining was performed for βh1 globin. In both cases robust expression is seen in the scattered erythroblasts of the FL in −/−, but not control mice.

FIG. 9F shows the expression of human β-globin locus genes for animals with the various BCL1 1A genotypes in the presence of the β-locus YAC transgene (YAC+) at E14.5 (n=4, 6, 4 for the fl/+, +/−, and −/− animals, respectively) and E18.5 (n=4, 7, 4). All γ- and β-globin levels for the different genotypes are significantly different (P<1×10$^{-5}$ by a two-sided t-test). All data are plotted as the mean±the standard deviation of the measurement.

FIG. 12A are examples of control (fl/+) and mutant mice (−/−) from the same litter at E18.5. Mice were obtained in expected Mendelian ratios at E18.5 and the mutants were morphologically indistinguishable from control littermates.

FIG. 12B are protein expression of BCL1 1A data assessed in E18.5 fetal livers and showed reduced expression in heterozygous animals, with absent expression in null animals. GAPDH was analyzed as a loading control.

FIG. 15A shows saggital sections are shown at low resolution and show that there are no gross histological abnormalities seen in these mice (at 5× magnification).

FIG. 15B shows histological sections stained with hematoxylin and eosin (H&E) are shown at two magnifications (10× objective with a 40× lens) from E14.5 and E18.5 fetal livers. These sections reveal clusters of erythroblasts within the fetal liver that appear to be similar in quantity and morphologically normal.

FIG. 16A shows the relative RNA expression of the β-like globin genes is shown for controls (BCL11A fl/+), heterozygous animals (BCL11A−/+), and null animals (BCL11A−/−) at E14.5 (n=10, 14, 11 for these groups, respectively). Additionally, the relative expression of BCL11A RNA is shown. The relative expression is normalized with respect to GAPDH (with GAPDH set to a value of 1). All data is shown as the mean±the standard error of the measurement.

FIG. 16B shows the relative RNA expression (normalized to GAPDH) of the β-like globin genes for controls, heterozygous animals, and null animals at E18.5 (n=9, 9, 7 for these groups, respectively). All data is shown as the mean±the standard deviation.

FIG. 18A displays the percentages for all the human β-like globin genes±the standard deviation at E14.5 in β-Locus mice crosses with BCL11A mutant mice.

FIG. 18B displays the percentages for all the human β-like globin genes±the standard deviation at E18.5, in β-Locus mice crosses with BCL11A mutant mice. All γ- and β-globin levels for the different genotypes are significantly different (P<1×10$^{-5}$ by a two-sided t-test).

DETAILED DESCRIPTION OF THE INVENTION

Figure 1A:
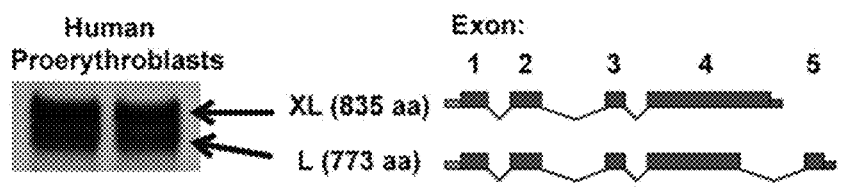
FIGS. 1A-1B show the expression of BCL11A in human erythroid progenitors.

The present invention provides for novel methods for the regulation of fetal hemoglobin (HbF) synthesis for the treatment of β-hemoglobinopathies and screening methods therein.

The invention is based upon identification of a novel function for the BCL11A protein, namely that the BCL11A protein acts as a stage specific regulator of fetal hemoglobin expression and that expression of BCL11A represses γ-globin induction. Accordingly, the invention provides novel methods for the regulation of γ-globin expression in erythroid cells. More specifically, these activities can be harnessed in methods for the treatment of β-hemoglobinopathies by induction of γ-globin via inhibition of the BCL11A gene product.

Fetal hemoglobin (HbF) is a tetramer of two adult α-globin polypeptides and two fetal β-like γ-globin polypeptides. During gestation, the duplicated γ-globin genes constitute the predominant genes transcribed from the β-globin locus. Following birth, γ-globin becomes progressively replaced by adult β-globin, a process referred to as the "fetal switch" (3). The molecular mechanisms underlying this switch have remained largely undefined and have been a subject of intense research. The developmental switch from production of predominantly fetal hemoglobin or HbF ($\alpha_2\gamma_2$) to production of adult hemoglobin or HbA ($\alpha_2\beta_2$) begins at about 28 to 34 weeks of gestation and continues shortly after birth at which point HbA becomes predominant. This switch results primarily from decreased transcription of the gamma-globin genes and increased transcription of beta-globin genes. On average, the blood of a normal adult contains only about 2% HbF, though residual HbF levels have a variance of over 20 fold in healthy adults (Atweh, Semin. Hematol. 38(4):367-73 (2001)).

Hemoglobinopathies encompass a number of anemias of genetic origin in which there is a decreased production and/or increased destruction (hemolysis) of red blood cells (RBCs). These disorders also include genetic defects that result in the production of abnormal hemoglobins with a concomitant impaired ability to maintain oxygen concentration. Some such disorders involve the failure to produce normal β-globin in sufficient amounts, while others involve the failure to produce normal β-globin entirely. These disorders specifically associated with the β-globin protein are referred to generally as β-hemoglobinopathies. For example, β-thalassemias result from a partial or complete defect in the expression of the β-globin gene, leading to deficient or absent HbA. Sickle cell anemia results from a point mutation in the β-globin structural gene, leading to the production of an abnormal (sickled) hemoglobin (HbS). HbS RBCs are more fragile than normal RBCs and undergo hemolysis more readily, leading eventually to anemia (Atweh, Semin. Hematol. 38(4):367-73 (2001)). Moreover, the presence of a BCL11A genetic variant, HBS1L-MYB variation, ameliorates the clinical severity in beta-thalassemia. This variant has been shown to be associated with HbF levels. Here, it was shown that there is an odds ratio of 5 for having a less severe form of beta-thalassemia with the high-HbF variant (Galanello S. et al., 2009, Blood, in press).

Recently, the search for treatment aimed at reduction of globin chain imbalance in patients with β-hemoglobinopathies has focused on the pharmacologic manipulation of fetal hemoglobin (α2γ2; HbF). The important therapeutic potential of such approaches is suggested by observations of the mild phenotype of individuals with co-inheritance of both homozygous β-thalassemia and hereditary persistence of fetal hemoglobin (HPFH), as well as by those patients with homozygous β°-thalassemia who synthesize no adult hemoglobin, but in whom a reduced requirement for transfusions is observed in the presence of increased concentrations of fetal hemoglobin. Furthermore, it has been observed that certain populations of adult patients with β chain abnormalities have higher than normal levels of fetal hemoglobin (HbF), and have been observed to have a milder clinical course of disease than patients with normal adult levels of HbF. For example, a group of Saudi Arabian sickle-cell anemia patients who express 20-30% HbF have only mild clinical manifestations of the disease (Pembrey, et al., Br. J. Haematol. 40: 415-429 (1978)). It is now accepted that β-hemoglobinopathies, such as sickle cell anemia and the β-thalassemias, are ameliorated by increased HbF production. (Reviewed in Jane and Cunningham Br. J. Haematol. 102: 415-422 (1998) and Bunn, N. Engl. J. Med. 328: 129-131 (1993)).

While the molecular mechanisms controlling the in vivo developmental switch from γ- to β-globin gene expression are currently unknown, there is accumulating evidence that external factors can influence γ-globin gene expression. The first group of compounds discovered having HbF reactivation activity were cytotoxic drugs. The ability to cause de novo synthesis of HbF by pharmacological manipulation was first shown using 5-azacytidine in experimental animals (DeSimone, Proc Natl Acad Sci USA. 79(14):4428-31 (1982)). Subsequent studies confirmed the ability of 5-azacytidine to increase HbF in patients with β-thalassemia and sickle cell disease (Ley, et al., N. Engl. J. Medicine, 307: 1469-1475 (1982), and Ley, et al., Blood 62: 370-380 (1983)). Additional experiments demonstrated that baboons treated with cytotoxic doses of arabinosylcytosine (ara-C) responded with striking elevations of F-reticulocytes (Papayannopoulou et al., Science. 224(4649):617-9 (1984)), and that treatment with hydroxyurea led to induction of γ-globin in monkeys or baboons (Letvin et. al., N Engl J Med. 310(14):869-73 (1984)).

The second group of compounds investigated for the ability to cause HbF reactivation activity was short chain fatty acids. The initial observation in fetal cord blood progenitor cells led to the discovery that γ-aminobutyric acid can act as a fetal hemoglobin inducer (Perrine et al., Biochem Biophys Res Commun. 148(2):694-700 (1987)). Subsequent studies showed that butyrate stimulated globin production in adult baboons (Constantoulakis et al., Blood. December; 72(6):1961-7 (1988)), and it induced γ-globin in erythroid progenitors in adult animals or patients with sickle cell anemia (Perrine et al., Blood. 74(1):454-9 (1989)). Derivatives of short chain fatty acids such as phenylbutyrate (Dover et al., Br J Haematol. 88(3):555-61 (1994)) and valproic acid (Liakopoulou et al., 1: Blood. 186(8):3227-35 (1995)) also have been shown to induce HbF in vivo. Given the large number of short chain fatty acid analogs or derivatives of this family, there are a number of potential compounds of this family more potent than butyrate. Phenylacetic and phenylalkyl acids (Torkelson et al., Blood Cells Mol Dis. 22(2):150-8. (1996)), which were discovered during subsequent studies, were considered potential HbF inducers as they belonged to this family of compounds. Presently, however, the use of butyrate or its analogs in sickle cell anemia and β-thalassemia remains experimental and cannot be recommended for treatment outside of clinical trials.

Clinical trials aimed at reactivation of fetal hemoglobin synthesis in sickle cell anemia and β-thalassemia have included short term and long term administration of such compounds as 5-azacytidine, hydroxyurea, recombinant human erythropoietin, and butyric acid analogs, as well as combinations of these agents. Following these studies, hydroxyurea was used for induction of HbF in humans and later became the first and only drug approved by the Food and Drug Administration (FDA) for the treatment of hemoglobinopathies. However, varying drawbacks have contraindicated the long term use of such agents or therapies, including unwanted side effects and variability in patient responses. For example, while hydroxyurea stimulates HbF production and has been shown to clinically reduce sickling crisis, it is potentially limited by myelotoxicity and the risk of carcinogenesis. Potential long term carcinogenicity would also exist in 5-azacytidine-based therapies. Erythropoietin-based therapies have not proved consistent among a range of patient populations. The short half-lives of butyric acid in vivo have been viewed as a potential obstacle in adapting these compounds for use in therapeutic interventions. Furthermore, very high dosages of butyric acid are necessary for inducing γ-globin gene expression, requiring catheritization for continuous infusion of the compound. Moreover, these high dosages of butyric acid can be associated with neurotoxicity and multiorgan damage (Blau, et al., Blood 81: 529-537 (1993)). While even minimal increases in HbF levels are helpful in sickle cell disease, β-thalassemias require a much higher increase that is not reliably, or safely, achieved by any of the currently used agents (Olivieri, Seminars in Hematology 33: 24-42 (1996)).

Identifying natural regulators of HbF induction and production could provide a means to devise therapeutic interventions that overcome the various drawbacks of the compounds described above. Recent genome-wide association studies have yielded insights into the genetic basis of numerous complex diseases and traits (McCarthy et al., Nat Rev Genet 9, 356 (2008) and Manolio et. al. J Clin Invest 118, 1590 (2008)). However, in the vast majority of instances, the functional link between a genetic association and the underlying pathophysiology remains to be uncovered. The level of fetal hemoglobin (HbF) is inherited as a quantitative trait and clinically important, given its above-mentioned and well-characterized role in ameliorating the severity of the principal β-hemoglobinopathies, sickle cell disease and β-thalassemia (Nathan et. al., Nathan and Oski's hematology of infancy and childhood ed. 6th, pp. 2 v. (xiv, 1864, xli p.) 2003)). Two genome-wide association studies have identified three major loci containing a set of five common single nucleotide polymorphisms (SNPs) that account for ~20% of the variation in HbF levels (Lettre et al., Proc Natl Acad Sci USA (2008); Uda et al., Proc Natl Acad Sci USA 105, 1620 (2008); Menzel et al., Nat Genet 39, 1197 (2007)). Moreover, several of these variants appear to predict the clinical severity of sickle cell disease (Lettre et al., Proc Natl Acad Sci USA (2008)) and at least one of these SNPs may also affect clinical outcome in β-thalassemia (Uda et al., Proc Natl Acad Sci USA 105, 1620 (2008)). The SNP with the largest effect size, explaining over 10% of the variation in HbF, is located in the second intron of a gene on chromosome 2, BCL11A. Whereas BCL11A, a C2H2-type zinc finger transcription factor, has been investigated for its role in lymphocyte development (Liu et al., Nat Immunol 4, 525 (2003) and Liu et al., Mol Cancer 5, 18 (2006)), its role in red blood cell production or globin gene regulation has not been previously assessed.

At the onset of the recombinant DNA era, studies of globin gene structure provided a strong molecular foundation for interrogating the fetal globin switch. Considerable effort has focused on delineating the cis-elements within the β-globin locus necessary for proper regulation of the genes within the β-like globin cluster. These studies relied on naturally occurring mutations and deletions that dramatically influence HbF levels in adults, and have been complemented by generation of transgenic mice harboring portions of the cluster (Nathan et. al., Nathan and Oski's hematology of infancy and childhood ed. 6th, pp. 2 v. (xiv, 1864, xli p.) 2003) and G. Stamatoyannopoulos, Exp Hematol 33, 259 (2005)). Although the precise cis-elements required for globin switching remain ill-defined, findings in transgenic mice have strongly indicated that the γ-globin genes are autonomously silenced in the adult stage, a finding that is most compatible with the absence of fetal-stage specific activators or the presence of a stage-specific repressor. The results of recent genetic association studies provide candidate genes to interrogate for their involvement in control of the γ-globin genes, such as BCL11A.

We identified a novel stage-specific repressor of the γ-globin genes, namely BCL11A, wherein the expression of the BCL11A protein acts as a negative regulator of expression from the γ-globin genes.

Methods of Increasing Fetal Hemoglobin in a Cell

The present invention provides improved methods for increasing fetal hemoglobin production in a cell, by the administration of compositions containing inhibitors of BCL11A. The data demonstrate that inhibition of BCL11A leads to increased expression from the γ-globin genes, and agents wherein to achieve this inhibition.

As disclosed herein, it is an object of the present invention to provide a method for increasing fetal hemoglobin levels in a cell.

Accordingly, one aspect of the invention provides a method for increasing fetal hemoglobin levels expressed by a cell, comprising the steps of contacting a hematopoietic progenitor cell with an effective amount of a composition comprising an inhibitor of BCL11A, whereby fetal hemoglobin expression is increased in the cell, or its progeny, relative to the cell prior to such contacting.

In connection with contacting a cell with an inhibitor of BCL11A, "increasing the fetal hemoglobin levels" in a cell indicates that fetal hemoglobin is at least 5% higher in populations treated with a BCL11A inhibitor, than in a comparable, control population, wherein no BCL11A inhibitor is present. It is preferred that the percentage of fetal hemoglobin expression in a BCL11A inhibitor treated population is at least 10% higher, at least 20% higher, at least 30% higher, at least 40% higher, at least 50% higher, at least 60% higher, at least 70% higher, at least 80% higher, at least 90% higher, at least 1-fold higher, at least 2-fold higher, at least 5-fold higher, at least 10 fold higher, at least 100 fold higher, at least 1000-fold higher, or more than a control treated population of comparable size and culture conditions. The term "control treated population" is used herein to describe a population of cells that has been treated with identical media, viral induction, nucleic acid sequences, temperature, confluency, flask size, pH, etc., with the exception of the addition of the BCL11A inhibitor.

An "inhibitor" of BCL11A, as the term is used herein, can function in a competitive or non-competitive manner, and can function, in one embodiment, by interfering with the expression of the BCL11A protein. Any of a number of different approaches can be taken to inhibit BCL11A expression or activity. A BCL11A inhibitor includes any chemical or biological entity that, upon treatment of a cell, results in inhibition of the biological activity caused by activation of BCL11A in response to cellular signals. BCL11A inhibitors, include, but are not limited to, small molecules, antibodies or antigen-binding antibody fragments, intrabodies, aptamers, antisense constructs, RNA interference agents, and ribozymes.

Antibody Inhibitors of BCL11A

Antibodies that specifically bind BCL11A can be used for the inhibition of the factor in vivo. Antibodies to BCL11A are commercially available and can be raised by one of skill in the art using well known methods. The BCL11A inhibitory activity of a given antibody, or, for that matter, any BCL11A inhibitor, can be assessed using methods known in the art or described herein—to avoid doubt, an antibody that inhibits BCL11A will cause an increase in fetal hemoglobin expression. Antibody inhibitors of BCL11A can include polyclonal and monoclonal antibodies and antigen-binding derivatives or fragments thereof. Well known antigen binding fragments include, for example, single domain antibodies (dAbs; which consist essentially of single VL or VH antibody domains), Fv fragment, including single chain Fv fragment (scFv), Fab fragment, and F(ab')2 fragment. Methods for the construction of such antibody molecules are well known in the art.

Nucleic Acid Inhibitors of BCL11A Expression

A powerful approach for inhibiting the expression of selected target polypeptides is through the use of RNA interference agents. RNA interference (RNAi) uses small interfering RNA (siRNA) duplexes that target the messenger RNA encoding the target polypeptide for selective degradation. siRNA-dependent post-transcriptional silencing of gene expression involves cleaving the target messenger RNA molecule at a site guided by the siRNA. "RNA interference (RNAi)" is an evolutionally conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18): 9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease will be of at least 10%, 20%, 30%, 40%, 50%, 60%, 70%, 80%, 90%, 95% or 99% or more as compared to the expression of a target gene or the activity or level of the protein encoded by a target gene which has not been targeted by an RNA interfering agent.

The terms "RNA interference agent" and "RNA interference" as they are used herein are intended to encompass those forms of gene silencing mediated by double-stranded RNA, regardless of whether the RNA interfering agent comprises an siRNA, miRNA, shRNA or other double-stranded RNA molecule. "Short interfering RNA" (siRNA), also referred to herein as "small interfering RNA" is defined as an RNA agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety). The target gene or sequence of the RNA interfering agent may be a cellular gene or genomic sequence, e.g. the BCL11A sequence. An siRNA may be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target. The siRNA preferably targets only one sequence. Each of the RNA interfering agents, such as siRNAs, can be screened for potential off-target effects by, for example, expression profiling. Such methods are known to one skilled in the art and are described, for example, in Jackson et al. Nature Biotechnology 6:635-637, 2003. In addition to expression profiling, one may also screen the potential target sequences for similar sequences in the sequence databases to identify potential sequences which may have off-target effects. For example, according to Jackson et al. (Id.), 15, or perhaps as few as 11 contiguous nucleotides, of sequence identity are sufficient to direct silencing of non-targeted transcripts. Therefore, one may initially screen the proposed siRNAs to avoid potential off-target silencing using the sequence identity analysis by any known sequence comparison methods, such as BLAST. siRNA sequences are chosen to maximize the uptake of the antisense (guide) strand of the siRNA into RISC and thereby maximize the ability of RISC to target human GGT mRNA for degradation. This can be accomplished by scanning for sequences that have the lowest free energy of binding at the 5'-terminus of the antisense strand. The lower free energy leads to an enhancement of the unwinding of the 5'-end of the antisense strand of the siRNA duplex, thereby ensuring that the antisense strand will be taken up by RISC and direct the sequence-specific cleavage of the human BCL11A mRNA. siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatizes with a variety of groups. Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases may also be modified. Any modified base useful for inhibiting or interfering with the expression of a target sequence may be used. For example, halogenated bases, such as 5-bromouracil and 5-iodouracil can be incorporated. The bases may also be alkylated, for example, 7-methylguanosine can be incorporated in place of a guanosine residue. Non-natural bases that yield successful inhibition can also be incorporated. The most preferred siRNA modifications include 2'-deoxy-2'-fluorouridine or locked nucleic acid (LAN) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA. The Examples herein provide specific examples of RNA interfering agents, such as shRNA molecules that effectively target BCL11A mRNA.

In a preferred embodiment, the RNA interference agent is delivered or administered in a pharmaceutically acceptable carrier. Additional carrier agents, such as liposomes, can be added to the pharmaceutically acceptable carrier. In another embodiment, the RNA interference agent is delivered by a vector encoding small hairpin RNA (shRNA) in a pharmaceutically acceptable carrier to the cells in an organ of an individual. The shRNA is converted by the cells after transcription into siRNA capable of targeting, for example, BCL11A.

In one embodiment, the vector is a regulatable vector, such as tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. In one embodiment, the RNA interference agents used in the methods described herein are taken up actively by cells in vivo following intravenous injection, e.g., hydrodynamic injection, without the use of a vector, illustrating efficient in vivo delivery of the RNA interfering agents. One method to deliver the siRNAs is catheterization of the blood supply vessel of the target organ. Other strategies for delivery of the RNA interference agents, e.g., the siRNAs or shRNAs used in the methods of the invention, may also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating into particles. The RNA interference agents, e.g., the siRNAs targeting BCL11A mRNA, may be delivered singly, or in combination with other RNA interference agents, e.g., siRNAs, such as, for example siRNAs directed to other cellular genes. BCL11A siRNAs may also be administered in combination with other pharmaceutical agents which are used to treat or prevent diseases or disorders associated with oxidative stress, especially respiratory diseases, and more especially asthma. Synthetic siRNA molecules, including shRNA molecules, can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) Nature 411:494-498; Elbashir, S. M., W. Lendeckel and T. Tuschl (2001) Genes & Development 15:188-200; Harborth, J. et al. (2001) J. Cell Science 114:4557-4565; Masters, J. R. et al. (2001) Proc. Natl. Acad. Sci., USA 98:8012-8017; and Tuschl, T. et al. (1999) Genes & Development 13:3191-3197). Alternatively, several commercial RNA synthesis suppliers are available including, but not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al. (2002) Genes Dev. 16:948-958; McManus, M. T. et al. (2002) RNA 8:842-850; Paul, C. P. et al. (2002) Nat. Biotechnol. 20:505-508; Miyagishi, M. et al. (2002) Nat. Biotechnol. 20:497-500; Sui, G. et al. (2002) Proc. Natl. Acad. Sci., USA 99:5515-5520; Brummelkamp, T. et al. (2002) Cancer Cell 2:243; Lee, N. S., et al. (2002) Nat. Biotechnol. 20:500-505; Yu, J. Y., et al. (2002) Proc. Natl. Acad. Sci., USA 99:6047-6052; Zeng, Y., et al. (2002) Mol. Cell 9:1327-1333; Rubinson, D. A., et al. (2003) Nat. Genet. 33:401-406; Stewart, S. A., et al. (2003) RNA 9:493-501). These vectors generally have a polIII promoter upstream of the dsRNA and can express sense and antisense RNA strands separately and/or as a hairpin structures. Within cells, Dicer processes the short hairpin RNA (shRNA) into effective siRNA. The targeted region of the siRNA molecule of the present invention can be selected from a given target gene sequence, e.g., a BCL11A coding sequence, beginning from about 25 to 50 nucleotides, from about 50 to 75 nucleotides, or from about 75 to 100 nucleotides downstream of the start codon. Nucleotide sequences may contain 5' or 3' UTRs and regions nearby the start codon. One method of designing a siRNA molecule of the present invention involves identifying the 23 nucleotide sequence motif AA(N19)TT (SEQ. ID. NO. 21) (where N can be any nucleotide) and selecting hits with at least 25%, 30%, 35%, 40%, 45%, 50%, 55%, 60%, 65%, 70% or 75% G/C content. The "TT" portion of the sequence is optional. Alternatively, if no such sequence is found, the search may be extended using the motif NA(N21), where N can be any nucleotide. In this situation, the 3' end of the sense siRNA may be converted to TT to allow for the generation of a symmetric duplex with respect to the sequence composition of the sense and antisense 3' overhangs. The antisense siRNA molecule may then be synthesized as the complement to nucleotide positions 1 to 21 of the 23 nucleotide sequence motif. The use of symmetric 3' TT overhangs may be advantageous to ensure that the small interfering ribonucleoprotein particles (siRNPs) are formed with approximately equal ratios of sense and antisense target RNA-cleaving siRNPs (Elbashir et al., (2001) supra and Elbashir et al., 2001 supra). Analysis of sequence databases, including but not limited to the NCBI, BLAST, Derwent and GenSeq as well as commercially available oligosynthesis companies such as OLIGOENGINE®, may also be used to select siRNA sequences against EST libraries to ensure that only one gene is targeted.

Delivery of RNA Interfering Agents

Methods of delivering RNA interference agents, e.g., an siRNA, or vectors containing an RNA interference agent, to the target cells, e.g., lymphocytes or other desired target cells, for uptake include injection of a composition containing the RNA interference agent, e.g., an siRNA, or directly contacting the cell, e.g., a lymphocyte, with a composition comprising an RNA interference agent, e.g., an siRNA. In another embodiment, RNA interference agent, e.g., an siRNA may be injected directly into any blood vessel, such as vein, artery, venule or arteriole, via, e.g., hydrodynamic injection or catheterization. Administration may be by a single injection or by two or more injections. The RNA interference agent is delivered in a pharmaceutically acceptable carrier. One or more RNA interference agent may be used simultaneously. In one preferred embodiment, only one siRNA that targets human BCL11A is used. In one embodiment, specific cells are targeted with RNA interference, limiting potential side effects of RNA interference caused by non-specific targeting of RNA interference. The method can use, for example, a complex or a fusion molecule comprising a cell targeting moiety and an RNA interference binding moiety that is used to deliver RNA interference effectively into cells. For example, an antibody-protamine fusion protein when mixed with siRNA, binds siRNA and selectively delivers the siRNA into cells expressing an antigen recognized by the antibody, resulting in silencing of gene expression only in those cells that express the antigen. The siRNA or RNA interference-inducing molecule binding moiety is a protein or a nucleic acid binding domain or fragment of a protein, and the binding moiety is fused to a portion of the targeting moiety. The location of the targeting moiety can be either in the carboxyl-terminal or amino-terminal end of the construct or in the middle of the fusion protein. A viral-mediated delivery mechanism can also be employed to deliver siRNAs to cells in vitro and in vivo as described in Xia, H. et al. (2002) Nat Biotechnol 20(10): 1006). Plasmid- or viral-mediated delivery mechanisms of shRNA may also be employed to deliver shRNAs to cells in vitro and in vivo as described in Rubinson, D. A., et al. ((2003) Nat. Genet. 33:401-406) and Stewart, S. A., et al. ((2003) RNA 9:493-501). The RNA interference agents, e.g., the siRNAs or shRNAs, can be introduced along with components that perform one or more of the following activities: enhance uptake of the RNA interfering agents, e.g., siRNA, by the cell, e.g., lymphocytes or other cells, inhibit annealing of single strands, stabilize single strands, or otherwise facilitate delivery to the target cell and increase inhibition of the target gene, e.g., BCL11A. The dose of the particular RNA interfering agent will be in an amount necessary to effect RNA interference, e.g., post translational gene silencing (PTGS), of the particular target gene, thereby leading to inhibition of target gene expression or inhibition of activity or level of the protein encoded by the target gene.

In one embodiment, the hematopoietic progenitor cell is contacted ex vivo or in vitro. In a specific embodiment, the cell being contacted is a cell of the erythroid lineage. In one embodiment, the composition inhibits BCL11A expression.

"Hematopoietic progenitor cell" as the term is used herein, refers to cells of a stem cell lineage that give rise to all the blood cell types including the myeloid (monocytes and macrophages, neutrophils, basophils, eosinophils, erythrocytes, megakaryocytes/platelets, dendritic cells), and the lymphoid lineages (T-cells, B-cells, NK-cells). A "cell of the erythroid lineage" indicates that the cell being contacted is a cell that undergoes erythropoiesis such that upon final differentiation it forms an erythrocyte or red blood cell (RBC). Such cells belong to one of three lineages, erythroid, lymphoid, and myeloid, originating from bone marrow haematopoietic progenitor cells. Upon exposure to specific growth factors and other components of the haematopoietic microenvironment, haematopoietic progenitor cells can mature through a series of intermediate differentiation cellular types, all intermediates of the erythroid lineage, into RBCs. Thus, cells of the "erythroid lineage", as the term is used herein, comprise hematopoietic progenitor cells, rubriblasts, prorubricytes, erythroblasts, metarubricytes, reticulocytes, and erythrocytes.

In some embodiment, the haematopoietic progenitor cell has at least one of the cell surface marker characteristic of haematopoietic progenitor cells: CD34+, CD59+, Thy1/CD90+, CD38$^{lo}$/−, and C-kit/CD117+. Preferably, the haematopoietic progenitor cells have several of these marker.

In some embodiment, the haematopoietic progenitor cells of the erythroid lineage have the cell surface marker characteristic of the erythroid lineage: CD71 and Ter119.

Stem cells, such as hematopoietic progenitor cells, are capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In one embodiment, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Generally, "progenitor cells" have a cellular phenotype that is more primitive (i.e., is at an earlier step along a developmental pathway or progression than is a fully differentiated cell). Often, progenitor cells also have significant or very high proliferative potential. Progenitor cells can give rise to multiple distinct differentiated cell types or to a single differentiated cell type, depending on the developmental pathway and on the environment in which the cells develop and differentiate.

In the context of cell ontogeny, the adjective "differentiated", or "differentiating" is a relative term. A "differentiated cell" is a cell that has progressed further down the developmental pathway than the cell it is being compared with. Thus, stem cells can differentiate to lineage-restricted precursor cells (such as a hematopoietic progenitor cell), which in turn can differentiate into other types of precursor cells further down the pathway (such as an erythrocyte precursor), and then to an end-stage differentiated cell, such as an erythrocyte, which plays a characteristic role in a certain tissue type, and may or may not retain the capacity to proliferate further.

In one embodiment, the inhibitor of BCL11A expression is selected from a small molecule and a nucleic acid. Alternatively, and preferably, the inhibitor of BCL11A expression is a BCL11A specific RNA interference agent, or a vector encoding said BCL11A specific RNA interference agent. In one specific embodiment, the RNA interference agent comprises one or more of the nucleotide sequences of SEQ ID NO: 1-6.

As used herein, the term "small molecule" refers to a chemical agent including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

A "nucleic acid", as described herein, can be RNA or DNA, and can be single or double stranded, and can be selected, for example, from a group including: nucleic acid encoding a protein of interest, oligonucleotides, nucleic acid analogues, for example peptide-nucleic acid (PNA), pseudo-complementary PNA (pc-PNA), locked nucleic acid (LNA) etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc.

As disclosed herein, it is an object of the present invention to provide a method for increasing fetal hemoglobin levels in a mammal.

Accordingly, one aspect of the present invention provides a method for increasing fetal hemoglobin levels in a mammal in need thereof, the method comprising the step of contacting a hematopoietic progenitor cell in the mammal with an effective amount of a composition comprising an inhibitor of BCL11A, whereby fetal hemoglobin expression is increased, relative to expression prior to such contacting.

In connection with contacting a cell in a mammal with an inhibitor of BCL11A, "increasing fetal hemoglobin levels in a mammal" indicates that fetal hemoglobin in the mammal is at least 5% higher in populations treated with a BCL11A inhibitor, than a comparable, control population, wherein no BCL11A inhibitor is present. It is preferred that the fetal hemoglobin expression in a BCL11A inhibitor treated mammal is at least 10% higher, at least 20% higher, at least 30% higher, at least 40% higher, at least 50% higher, at least 60% higher, at least 70% higher, at least 80% higher, at least 90% higher, at least 1-fold higher, at least 2-fold higher, at least 5-fold higher, at least 10 fold higher, at least 100 fold higher, at least 1000-fold higher, or more than a comparable control treated mammal. The term "comparable control treated mammal" is used herein to describe a mammal that has been treated identically, with the exception of the addition of the BCL11A inhibitor.

The term "mammal" is intended to encompass a singular "mammal" and plural "mammals," and includes, but is not limited to humans; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and bears. In some preferred embodiments, a mammal is a human.

Accordingly, in one embodiment, the mammal has been diagnosed with a hemoglobinopathy. In a further embodiment, the hemoglobinopathy is a β-hemoglobinopathy. In one preferred embodiment, the hemoglobinopathy is a sickle cell disease. As used herein, "sickle cell disease" can be sickle cell anemia, sickle-hemoglobin C disease (HbSC), sickle beta-plus-thalassaemia (HbS/β+), or sickle beta-zero-thalassaemia (HbS/β0). In another preferred embodiment, the hemoglobinopathy is a β-thalassemia.

As used herein, the term "hemoglobinopathy" means any defect in the structure or function of any hemoglobin of an individual, and includes defects in the primary, secondary, tertiary or quaternary structure of hemoglobin caused by any mutation, such as deletion mutations or substitution mutations in the coding regions of the β-globin gene, or mutations in, or deletions of, the promoters or enhancers of such genes that cause a reduction in the amount of hemoglobin produced as compared to a normal or standard condition. The term further includes any decrease in the amount or effectiveness of hemoglobin, whether normal or abnormal, caused by external factors such as disease, chemotherapy, toxins, poisons, or the like.

The term "effective amount", as used herein, refers to the amount that is safe and sufficient to treat, lesson the likelihood of, or delay the development of a hemoglobinopathy. The amount can thus cure or result in amelioration of the symptoms of the hemoglobinopathy, slow the course of hemoglobinopathy disease progression, slow or inhibit a symptom of a hemoglobinopathy, slow or inhibit the establishment of secondary symptoms of a hemoglobinopathy or inhibit the development of a secondary symptom of a hemoglobinopathy. The effective amount for the treatment of the hemoglobinopathy depends on the type of hemoglobinopathy to be treated, the severity of the symptoms, the subject being treated, the age and general condition of the subject, the mode of administration and so forth. Thus, it is not possible or prudent to specify an exact "effective amount". However, for any given case, an appropriate "effective amount" can be determined by one of ordinary skill in the art using only routine experimentation.

The treatment according to the present invention ameliorates one or more symptoms associated with the disorder by increasing the amount of fetal hemoglobin in the individual. Symptoms typically associated with a hemoglobinopathy, include for example, anemia, tissue hypoxia, organ dysfunction, abnormal hematocrit values, ineffective erythropoiesis, abnormal reticulocyte (erythrocyte) count, abnormal iron load, the presence of ring sideroblasts, splenomegaly, hepatomegaly, impaired peripheral blood flow, dyspnea, increased hemolysis, jaundice, anemic pain crises, acute chest syndrome, splenic sequestration, priapism, stroke, hand-foot syndrome, and pain such as angina pectoris.

In one embodiment, the hematopoietic progenitor cell is contacted ex vivo or in vitro, and the cell or its progeny is administered to said mammal. In a further embodiment, the hematopoietic progenitor cell is a cell of the erythroid lineage.

In one embodiment, the hematopoietic progenitor cell is contacted with a composition comprising of an inhibitor of BCL11A and a pharmaceutically acceptable carrier or diluent. In one embodiment, said composition is administered by injection, infusion, instillation, or ingestion.

As used herein, the term "pharmaceutically acceptable", and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. Each carrier must also be "acceptable" in the sense of being compatible with the other ingredients of the formulation. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. The pharmaceutical formulation contains a compound of the invention in combination with one or more pharmaceutically acceptable ingredients. The carrier can be in the form of a solid, semi-solid or liquid diluent, cream or a capsule. Typically, such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques. The phrase "pharmaceutically acceptable carrier or diluent" means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body.

As used herein, "administered" refers to the placement of an inhibitor of BCL11A into a subject by a method or route which results in at least partial localization of the inhibitor at a desired site. An agent which inhibits BCL11A can be administered by any appropriate route which results in effective treatment in the subject, i.e. administration results in delivery to a desired location in the subject where at least a portion of the composition delivered, i.e. at least one agent which inhibits BCL11A, is active in the desired site for a period of time. The period of time the inhibitor is active depends on the half-life in vivo after administration to a subject, and can be as short as a few hours, e. g. twenty-four hours, to a few days, to as long as several years. Modes of administration include injection, infusion, instillation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

In one embodiment, the hematopoietic progenitor cell from a mammal needing treatment is contacted with a composition that inhibits BCL11A expression.

By "inhibits BCL11A expression" is meant that the amount of expression of BCL11A is at least 5% lower in populations treated with a BCL11A inhibitor, than a comparable, control population, wherein no BCL11A inhibitor is present. It is preferred that the percentage of BCL11A expression in a BCL11A inhibitor treated population is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population in which no BCL11A inhibitor is added.

In one embodiment, the inhibitor of BCL11A expression is selected from a small molecule and a nucleic acid. In a preferred embodiment, the nucleic acid is a BCL11A specific RNA interference agent or a vector encoding said RNA interference agent, or an aptamer that binds BCL11A. In a preferred embodiment, said RNA interference agent comprises one or more of the nucleotide sequences of SEQ ID NO:1-6.

In one embodiment, the hematopoietic progenitor cell from a mammal needing treatment is contacted with a composition that inhibits BCL11A activity.

By "inhibits BCL11A activity" is meant that the amount of functional activity of BCL11A is at least 5% lower in populations treated with a BCL11A inhibitor, than a comparable, control population, wherein no BCL11A inhibitor is present. It is preferred that the percentage of BCL11A activity in a BCL11A-inhibitor treated population is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population in which no BCL11A inhibitor is added. At a minimum, BCL11A activity can be assayed by determining the amount of BCL11A expression at the protein or mRNA levels, using techniques standard in the art. Alternatively, or in addition, BCL11A activity can be determined using a reporter construct, wherein the reporter construct is sensitive to BCL11A activity. The γ-globin locus sequence is recognizable by the nucleic acid-binding motif of the BCL11A construct. Alternatively, or in addition, BCL11A activity can be assayed by measuring fetal hemoglobin expression at the mRNA or protein level following treatment with a candidate BCL11A inhibitor. An increase in fetal hemoglobin expression of at least 10% is indicative of a compound being a candidate BCL11A inhibitor.

In one embodiment, the inhibitor of BCL11A activity is selected from the group consisting of an antibody against BCL11A or an antigen-binding fragment thereof, a small molecule, and a nucleic acid. In one preferred embodiment, the nucleic acid is a BCL11A specific RNA interference agent, a vector encoding the RNA interference agent, or an aptamer that binds BCL11A. In another preferred embodiment, the RNA interference agent comprises one or more of the nucleotide sequences of SEQ ID NO: 1-6.

An "antibody" that can be used according to the methods described herein includes complete immunoglobulins, antigen binding fragments of immunoglobulins, as well as antigen binding proteins that comprise antigen binding domains of immunoglobulins. Antigen binding fragments of immunoglobulins include, for example, Fab, Fab', F(ab')$_2$, scFv and dAbs. Modified antibody formats have been developed which retain binding specificity, but have other characteristics that may be desirable, including for example, bispecificity, multivalence (more than two binding sites), and compact size (e.g., binding domains alone). Single chain antibodies lack some or all of the constant domains of the whole antibodies from which they are derived. Therefore, they can overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and can have greater permeability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies. Multiple single chain antibodies, each single chain having one VH and one VL domain covalently linked by a first peptide linker, can be covalently linked by at least one or more peptide linker to form multivalent single chain antibodies, which can be monospecific or multispecific. Each chain of a multivalent single chain antibody includes a variable light chain fragment and a variable heavy chain fragment, and is linked by a peptide linker to at least one other chain. The peptide linker is composed of at least fifteen amino acid residues. The maximum number of linker amino acid residues is approximately one hundred. Two single chain antibodies can be combined to form a diabody, also known as a bivalent dimer. Diabodies have two chains and two binding sites, and can be monospecific or bispecific. Each chain of the diabody includes a VH domain connected to a VL domain. The domains are connected with linkers that are short enough to prevent pairing between domains on the same chain, thus driving the pairing between complementary domains on different chains to recreate the two antigen-binding sites. Three single chain antibodies can be combined to form triabodies, also known as trivalent trimers. Triabodies are constructed with the amino acid terminus of a VL or VH domain directly fused to the carboxyl terminus of a VL or VH domain, i.e., without any linker sequence. The triabody has three Fv heads with the polypeptides arranged in a cyclic, head-to-tail fashion. A possible conformation of the triabody is planar with the three binding sites located in a plane at an angle of 120 degrees from one another. Triabodies can be monospecific, bispecific or trispecific. Thus, antibodies useful in the methods described herein include, but are not limited to, naturally occurring antibodies, bivalent fragments such as (Fab')2, monovalent fragments such as Fab, single chain antibodies, single chain Fv (scFv), single domain antibodies, multivalent single chain antibodies, diabodies, triabodies, and the like that bind specifically with an antigen.

Antibodies can also be raised against a polypeptide or portion of a polypeptide by methods known to those skilled in the art. Antibodies are readily raised in animals such as rabbits or mice by immunization with the gene product, or a fragment thereof. Immunized mice are particularly useful for providing sources of B cells for the manufacture of hybridomas, which in turn are cultured to produce large quantities of monoclonal antibodies. Antibody manufacture methods are described in detail, for example, in Harlow et al., 1988. While both polyclonal and monoclonal antibodies can be used in the methods described herein, it is preferred that a monoclonal antibody is used where conditions require increased specificity for a particular protein.

In one embodiment, the inhibitor of BCL11A activity interferes with BCL11A interactions with BCL11A binding partners. In one embodiment, the binding partners are GATA-1, FOG-1, and components of the NuRD complex. In another embodiment, the binding partners are matrin-3, MTA2 and RBBP7.

By "interferes with BCL11A interactions with BCL11A binding partners" is meant that the amount of interaction of BCL11A with the BCL11A binding partner is at least 5% lower in populations treated with a BCL11A inhibitor, than a comparable, control population, wherein no BCL11A inhibitor is present. It is preferred that the amount of interaction of BCL11A with the BCL11A binding partner in a BCL11A-inhibitor treated population is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population in which no BCL11A inhibitor is added. At a minimum, BCL11A interaction can be assayed by determining the amount of BCL11A binding to the BCL11A binding partner using techniques standard in the art, including, but not limited to, mass spectrometry, immunoprecipitation, or gel filtration assays. Alternatively, or in addition, BCL11A activity can be assayed by measuring fetal hemoglobin expression at the mRNA or protein level following treatment with a candidate BCL11A inhibitor.

In one embodiment, BCL11A activity is the interaction of BCL11A with its binding partners: GATA-1, FOG-1, components of the NuRD complex, matrin-3, MTA2 and RBBP7. Accordingly, any antibody or fragment thereof, small molecule, chemical or compound that can block this interaction is considered an inhibitor of BCL11A activity.

In one embodiment, any method known it he art can be used to measure an increase in fetal hemoglobin expression, e. g. Western Blot analysis of fetal γ-globin protein and quantifying mRNA of fetal γ-globin.

As disclosed herein, also encompassed within the objects of the present invention are methods for screening for modulators of BCL11A activity or expression for the identification of inhibitors of BCL11A.

Accordingly, one aspect of the present invention provides for a method for identifying a modulator of BCL11A activity or expression, the method comprising contacting a hematopoietic progenitor cell with a composition comprising a test compound, and measuring the level of fetal hemoglobin or fetal hemoglobin mRNA in said cell or its progeny, wherein an increase in fetal hemoglobin is indicative that said test compound is a candidate inhibitor of BCL11A activity or expression.

In one embodiment, the hematopoietic progenitor cell is contacted in vivo, ex vivo, or in vitro. In one embodiment, the cell is of human, non-human primate, or mammalian origin. In one embodiment, the test compound is a small molecule, antibody or nucleic acid. In one embodiment, the composition causes an increase in fetal hemoglobin expression.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

As used herein, the term "vector" refers to a nucleic acid molecule capable of transporting another nucleic acid to which it has been linked. One type of vector is a "plasmid", which refers to a circular double stranded DNA loop into which additional nucleic acid segments can be ligated. Another type of vector is a viral vector; wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors", or more simply "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, lentiviruses, adenoviruses and adeno-associated viruses), which serve equivalent functions. In one embodiment, lentiviruses are used to deliver one or more siRNA molecule of the present invention to a cell.

Within an expression vector, "operably linked" is intended to mean that the nucleotide sequence of interest is linked to the regulatory sequence(s) in a manner which allows for expression of the nucleotide sequence (e.g., in an in vitro transcription/translation system or in a target cell when the vector is introduced into the target cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). Furthermore, the RNA interfering agents may be delivered by way of a vector comprising a regulatory sequence to direct synthesis of the siRNAs of the invention at specific intervals, or over a specific time period. It will be appreciated by those skilled in the art that the design of the expression vector can depend on such factors as the choice of the target cell, the level of expression of siRNA desired, and the like.

The expression vectors of the invention can be introduced into target cells to thereby produce siRNA molecules of the present invention. In one embodiment, a DNA template, e.g., a DNA template encoding the siRNA molecule directed against the mutant allele, may be ligated into an expression vector under the control of RNA polymerase III (Pol III), and delivered to a target cell. Pol III directs the synthesis of small, noncoding transcripts which 3' ends are defined by termination within a stretch of 4-5 thymidines. Accordingly, DNA templates may be used to synthesize, in vivo, both sense and antisense strands of siRNAs which effect RNAi (Sui, et al. (2002) PNAS 99(8):5515).

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

The present invention can be defined in any of the following alphabetized paragraphs:

[A] A method for increasing fetal hemoglobin levels in a cell, the method comprising the steps of contacting a hematopoietic progenitor cell with an effective amount of a composition comprising an inhibitor of BCL11A, whereby fetal hemoglobin expression is increased in said cell, or its progeny, relative to the cell prior to said contacting.

[B] The method of paragraph [A], wherein the hematopoietic progenitor cell is a cell of the erythroid lineage.

[C] The method of paragraph [A], wherein the hematopoietic progenitor cell is contacted ex vivo or in vitro.

[D] The method of paragraph [A], wherein the composition comprising an inhibitor of BCL11A inhibits BCL11A expression.

[E] The method of paragraph [D], wherein the inhibitor of BCL11A expression is selected from a small molecule and a nucleic acid.

[F] The method of paragraph [E], wherein the nucleic acid is a BCL11A specific RNA interference agent, or a vector encoding a BCL11A specific RNA interference agent.

[G] The method of paragraph [F], wherein the RNA interference agent comprises one or more of the nucleotide sequences of SEQ ID NO:1-6.

[H] The method of paragraph [A], wherein the composition comprising an inhibitor of BCL11A inhibits BCL11A activity.

[I] The method of paragraph [H], wherein the inhibitor of BCL11A activity is selected from the group consisting of an antibody against BCL11A or an antigen-binding fragment thereof, a small molecule, and a nucleic acid.

[J] The method of paragraph [I], wherein the nucleic acid is a BCL11A specific RNA interference agent, a vector encoding a RNA interference agent, or an a tamer that binds BCL11A.

[K] The method of paragraph [J], wherein the RNA interference agent comprises one or more of the nucleotide sequences of SEQ ID NO:1-6.

[L] A method for increasing fetal hemoglobin levels in a mammal in need thereof, the method comprising the step of contacting a hematopoietic progenitor cell in said mammal with an effective amount of a composition comprising an inhibitor of BCL11A, whereby fetal hemoglobin expression is increased in said mammal, relative to expression prior to said contacting.

[M] The method of paragraph [L], wherein the mammal has been diagnosed with a hemoglobinopathy.

[N] The method of paragraph [M], wherein the hemoglobinopathy is a β-hemoglobinopathy.

[O] The method of paragraph [M], wherein the hemoglobinopathy is sickle cell disease.

[P] The method of paragraph [M], wherein the hemoglobinopathy is β-thalassemia.

[Q] The method of paragraph [L], wherein the hematopoietic progenitor cell is contacted ex vivo or in vitro, and said cell or its progeny is administered to said mammal.

[R] The method of paragraph [L], wherein the contacting comprises contacting said cell with a composition comprising of an inhibitor of BCL11A and a pharmaceutically acceptable carrier or diluent.

[S] The method of paragraph [L], wherein the composition is administered by injection, infusion, instillation, or ingestion.

[T] The method of paragraph [L], wherein the composition comprising an inhibitor of BCL11A inhibits BCL11A expression.

[U] The method of paragraph [T], wherein the inhibitor of BCL11A expression is selected from a small molecule and a nucleic acid.

[V] The method of paragraph [U], wherein the nucleic acid is a BCL11A specific RNA interference agent or a vector encoding a RNA interference agent, or an a tamer that binds BCL11A.

[W] The method of paragraph [V], wherein the RNA interference agent comprises one or more of the nucleotide sequences of SEQ ID NO:1-6.

[X] The method of paragraph [L], wherein the composition comprising an inhibitor of BCL11A inhibits BCL11A activity.

[Y] The method of paragraph [X], wherein the inhibitor of BCL11A activity is selected from the group consisting of an antibody against BCL11A or an antigen-binding fragment thereof, a small molecule, and a nucleic acid.

[Z] The method of paragraph [Y], wherein the nucleic acid is a BCL11A specific RNA interference agent, a vector encoding said RNA interference agent, or an a tamer that binds BCL11A.

[AA] The method of paragraph [Z], wherein the RNA interference agent comprises one or more of the nucleotide sequences of SEQ ID NO:1-6.

[BB] A method for identifying a modulator of BCL11A activity or expression, the method comprising contacting a hematopoietic progenitor cell with a composition comprising a test compound, and measuring the level of fetal hemoglobin or fetal hemoglobin mRNA in said cell or its progeny, wherein an increase in fetal hemoglobin is indicative that said test compound is a candidate inhibitor of BCL11A activity or expression.

[CC] The method of paragraph [AA], wherein the hematopoietic progenitor cell is contacted in vivo, ex vivo, or in vitro.

[DD] The method of paragraph [AA], wherein the cell is of human, non-human primate, or mammalian origin.

[EE] The method of paragraph [AA], wherein the test compound is a small molecule, antibody or nucleic acid.

[FF] The method of paragraph [AA], wherein the composition causes an increase in fetal hemoglobin mRNA or protein expression.

This invention is further illustrated by the following example which should not be construed as limiting. The contents of all references cited throughout this application, as well as the figures and table are incorporated herein by reference.

Example 1

Materials and Methods

Cell Culture

Mouse erythroleukemia (MEL) cells were cultured and subclones carrying the BirA enzyme and tagged versions of BCL11A were created as previously described (Woo et al., Mol Cell Biol 28, 2675 (2008)). All constructs were created using standard recombinant DNA techniques. MEL cells were maintained in Dulbecco's modified Eagle's medium (DMEM) with 10% fetal calf serum (FCS) and 2% penicillin-streptomycin (P/S). Appropriate antibiotics were added to the medium as necessary for selection or maintenance of clones, as described (Woo et al., Mol Cell Biol 28, 2675 (2008)).

COS-7 and 293T cells were maintained in DMEM with 10% FCS. These cells were transfected with the FuGene 6 (Roche) reagent according to manufacturer's protocol.

Primary human CD34+ cells were obtained from magnetically-sorted mononuclear samples of G-CSF mobilized peripheral blood from donors and were frozen down after isolation. Cells were obtained from the Yale Center of Excellence in Molecular Hematology (YCEMH). Cells were thawed and washed into RPMI 1640 with 10% FCS, and then seeded in StemSpan SFEM Medium (StemCell Technologies Inc.) with 1×CC100 cytokine mix (StemCell Technologies Inc.) and 2% P/S. Cells were maintained in this expansion medium at a density of $0.1-1\times10^6$ cells/ml with media changes every other or every third day as necessary. Cells were kept in expansion medium for a total of 6 days. On day 6, cells were reseeded into StemSpan SFEM Medium with 2% P/S, 20 ng/ml SCF, 1 U/ml Epo, 5 ng/ml IL-3, 2 micromolar dexamethasone, and 1 micromolar β-estradiol. Cells were maintained in differentiation medium, with media changes every other or every third day as needed. Cells were maintained at a density of $0.1-1\times10^6$ cells/ml. By day 3 of differentiation, homogeneous larger blasts were present in the culture. By day 5, the majority of cells had proerythroblast morphology and on day 7 the majority of the cells had basophilic erythroblast morphology. By day 12 of differentiation, the majority of cells were of orthochromatophilic and polychromatophilic erythroblast morphology.

Hemolysates were prepared from cells on day 12 of differentiation, as has been described (Sankaran et al., Genes Dev. 22:463 (2008)), using osmotic lysis in water and three rapid freeze-thaw cycles. Debris were cleared by centrifugation and the lysates were stored at −80° C. or for a few days at 4° C. Hemoglobin electrophoresis with cellulose acetate and high performance liquid chromatography (HPLC) were carried out in the clinical laboratories of the Brigham and Women's Hospital using clinically-calibrated standards for the human hemoglobins.

RNA Extraction and qRT-PCR

Isolation of RNA was performed using the Trizol reagent (Sigma) or with the RNeasy Mini Kit (Qiagen). RNA obtained using the Trizol reagent method was subsequently treated with the RQ1 DNase (Promega) before cDNA synthesis occurred. An on-column DNase (Qiagen) digestion was performed according to manufacturer's instructions with the RNeasy Mini Kit. cDNA was synthesized with the iScript cDNA synthesis Kit (Bio-Rad). Real-time PCR was performed using the iQ SYBR Green Mastermix (Bio-Rad), as described previously (Sankaran et al., Genes Dev. 22:463 (2008)). Relative expression was quantitated using the ΔΔCt method as described previously (Sankaran et al., Genes Dev 22, 463 (2008)). Sequences of primers used for RT-PCR are available on request. Preparation of samples for expression microarray analysis was done as previously described (Sankaran et al., Genes Dev 22, 463 (2008)) and microarrays were process by the Dana-Farber Cancer Institute Microarray Core Facility. Data processing was performed using dChip at the Harvard University World Wide Web site computer lab and at the r-project organization World Wide Web site) with filtering performed as described previously (Sankaran et. al., Genes Dev 22, 463 (2008); Mootha et al., Nat Genet 34, 267 (2003); Su et al., Proc. Natl. Acad. Sci. U.S.A. 101:6062 (2004); and Su et al., Proc. Natl. Acad. Sci. U.S.A. 99:4465 (2002)). Since prior work had suggested that Affymetrix average difference levels of <100 for at least one sample represent RNAs that are unlikely to be expressed (Su et al., Proc. Natl. Acad. Sci. U.S.A. 99:4465 (2002)), this was used as the filtering criteria for all analyses performed here.

Proteomic Analysis

Analysis of protein interaction partners using affinity tagged versions of BCL11A was performed as previously described (Woo et al., Mol. Cell. Biol. 28:2675 (2008)). Mass spectrometric analysis was performed at the Taplin Biological Mass Spectrometry Facility at Harvard Medical School. Following identification of peptides in individual samples (with three samples submitted per gel lane), redundancy was collapsed. A subtractive approach was then employed to identify proteins that were specifically purified in the BCL11A pulldowns and not in the control pulldowns in the parental MEL cell lines containing the BirA enzyme. Data were then consolidated by identifying proteins that were common in independent experiments. All nuclear extract (NE) preparations, candidate immunoprecipitations (IPs), gel filtration of NEs, transient exogenous expression with IPs, and mapping studies were carried out using methods that have been described previously (Woo et al., Mol Cell Biol 28, 2675 (2008)).

siRNA and shRNA Knockdown

Pooled siRNAs samples were obtained from Dharmacon. This included a non-targeting pool (D-001810-10) and a BCL11A targeting pool (L-006996-00). The BCL11A siRNA target sequences used are presented in Table 1.

TABLE 1

| SEQ ID NO 1 | GAGCACAAACGGAAACAAU |
| SEQ ID NO 2 | GCCACAGGAUGACGAUUGU |
| SEQ ID NO 3 | GCACUUAAGCAAACGGGAA |
| SEQ ID NO 4 | ACAGAACACUCAUGGAUUA |

These siRNAs were prepared as 100 µM stocks, as recommended by the manufacturer. Aliquots were stored at −80° C. until use. siRNAs were introduced into expanded and differentiating CD34 cells using the Microporator-Mini (Digital Bio Technology). Manufacturer's protocols were followed and after screening a number of conditions, it was found that with a single pulse of 1800 V (using a pulse width of 20 ms) the best transduction efficiency was obtained, as assessed using a GFP reporter plasmid. Transduction efficiency was estimated to be ~50-60% of viable cells. Typically, ~250,000 cells were transduced with 4 µl of siRNAs in a volume of ~15 µl. Cells were then seeded into fresh differentiation medium.

shRNA clones in the pLKO vector were obtained from a large collection of shRNAs that has been previously described (Moffat et al., Cell 124:1283 (2006)). Two shRNAs targeting BCL11A were obtained with the sequences presented Table 2:

```
                                                SEQ ID NO 5
CCGGCGCACAGAACACTCATGGATTCTCGAGAATCCATGAGTGTTCTGTG

CGTTTTTG
                                                SEQ ID NO 6
CCGGCCAGAGGATGACGATTGTTTACTCGAGTAAACAATCGTCATCCTCT

GGTTTTTG
```

These shRNAs were chosen, since they target both of the major isoforms of BCL11A found in erythroid cells. Lentiviruses were prepared and infection of cells was carried out as described (Moffat et al., Cell 124:1283 (2006)). The cells were washed twice with PBS and media was changed 24 hours after the infection. Selection with puromycin was initiated at 48 hours following infection, which generally corresponded to the time when the cells were seeded into differentiation medium.

Results

Inverse Correlation of BCL11A and HbF Levels

Figure 1B:
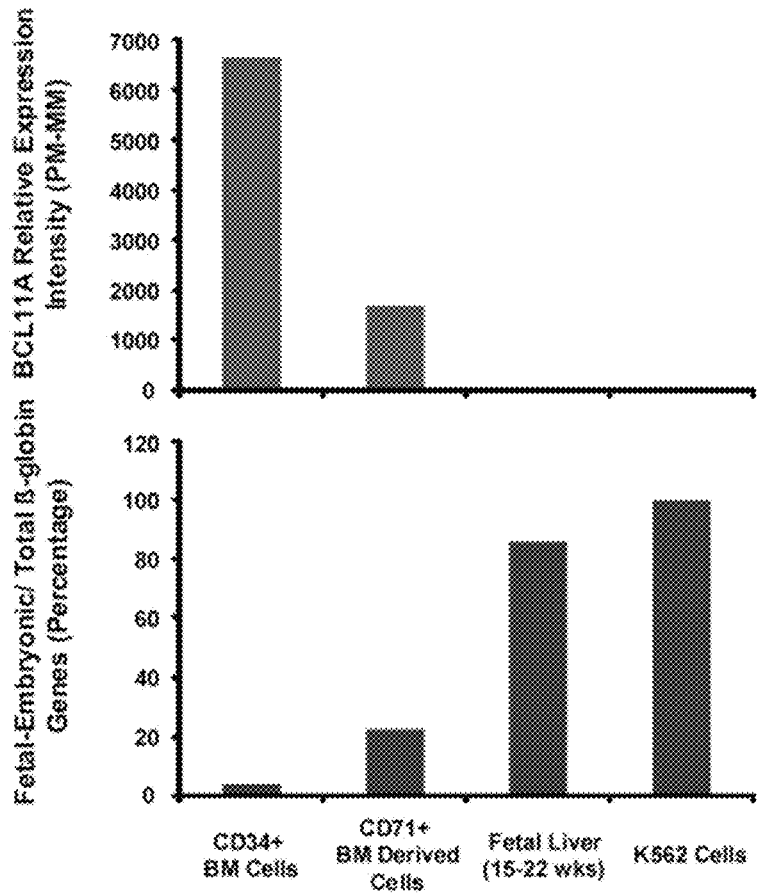

As a first step in seeking how variation at the BCL11A locus might relate to globin expression, expression of BCL11A in erythroid cells was examined. In primary adult human erythroid cells, BCL11A is expressed as two major isoforms at the protein and RNA levels (FIG. 1A). These isoforms have been previously designated isoforms 1 and 2 or XL and L (Liu et al., Mol Cancer 5, 18 (2006)). The XL and L isoforms differ only in usage of the 3' terminal exon and appear to bind one another and function similarly in other settings (Liu et al., Mol. Cancer 5, 18 (2006)). A western blot shows the major isoforms, XL and L, from nuclear extracts of human erythroid cells (A). These two isoforms, which could also be confirmed by RT-PCR of all known and predicted exons, are depicted on the right hand side of this panel with the appropriate exon numbers shown above the diagram. Interrogation of the expression pattern of BCL11A in a collection of expression data from human cells (Su et al., Proc. Natl. Acad. Sci. U.S.A. 101:6062 (2004)) reveals an inverse correlation between the expression of BCL11A and that of the β-globin gene in cells of the erythroid lineage (FIG. 1B). The expression of BCL11A in erythroid cells at different stages of human ontogeny and with varying patterns of globin gene expression are shown (FIG. 1B), as assessed from a large collection of expression data in human tissues and cell types (Su et al., Proc. Natl. Acad. Sci. U.S.A. 101:6062 (2004)). The top panel shows the normalized expression (across a panel of 79 human cell types, performed at least in duplicate for each cell type) of BCL11A in the different erythroid cell types and stages listed at the bottom from probe 219497_s_at. Similar results were seen with BCL11A probes 219498_s_at and 210347_s_at. The bottom panel shows the normalized levels of fetal and embryonic human globins from this dataset. The data were normalized as for the top panel and then relative percentages were calculated based upon all of the human β-globin genes (including the ε-, γ-, δ- and β-globin genes). Notably, BCL11A expression is very low in fetal liver erythroid cells and in the embryonic erythroid cell line K562. The inverse correlation indicates that BCL11A expression is developmentally stage-restricted. Furthermore, the temporal pattern is consistent with BCL11A acting as a potential repressor of γ-globin expression.

Figure 2A:
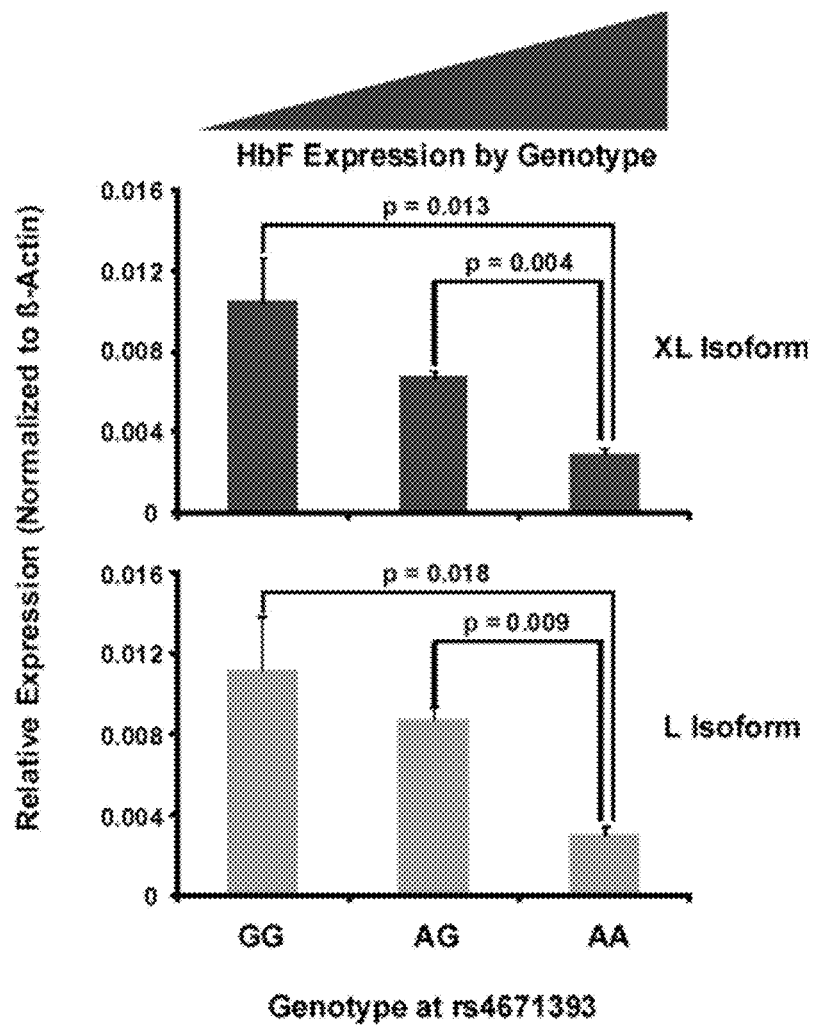
FIG. 2A demonstrates that the common variant rs4671393 is associated with BCL11A expression in human lymphoblastoid cell lines from the HapMap European (CEU) and African (YRI) populations.

Genetic variants in intron 2 of the BCL11A gene are significantly associated with HbF levels in normal individuals and patients with hemoglobin disorders (Lettre et al., Proc. Natl. Acad. Sci. U.S.A. (2008); Uda et al., Proc. Natl. Acad. Sci. USA 105:1620 (2008); and Menzel et al., Nat. Genet. 39, 1197 (2007)). The association signal has been recently finely mapped to a single variant that is in close linkage disequilibrium (LD) with the SNP rs4671393 (Lettre et al., supra (2008)). Since this association has been confirmed in multiple independent European and African diasporic populations, expression of BCL11A as a function of the genotype at rs4671393 in lymphoblastoid cell lines from the HapMap European (CEU) and African (YRI) groups was examined. As shown in FIG. 2A, the common variant rs4671393 is associated with BCL11A expression in human lymphoblastoid cell lines from the HapMap European (CEU) and African (YRI) populations. qRT-PCR was performed on RNA from these cell lines and normalized to the level of human β-actin. Two separate PCR reactions were performed that could individually assess levels of the XL (Top) and L (Bottom) isoforms based on differences at the 3' end of these genes. Similar results were obtained by analyzing common 5' sequences using qRT PCR. Results are depicted as the mean with the standard error shown by error bars. Differences between genotypes were calculated using the Student t-test. The pattern of increase in HbF levels for each of these genotypes is shown at the top (Lettre et al., Proc Natl Acad Sci USA (2008)).

A striking difference was observed in expression for both the XL and L isoforms between individuals homozygous for the low HbF allele (GG), heterozygous for both alleles, or homozygous for the minor allele associated with high HbF levels (AA) (FIG. 2A). Cells homozygous for the "high HbF" alleles expressed a lower level of BCL11A transcripts than those homozygous for "low HbF" alleles or heterozygous for both alleles. Thus, expression of BCL11A at the different human variants is inversely correlated with the associated HbF levels. The difference in expression between the "high" and "low" HbF associated BCL11A alleles is roughly 3-fold. Hence, relatively modest differences in BCL11A expression appear to associate with changes in HbF expression. Taken together with the developmental pattern of expression of BCL11A, these results provide independent, yet indirect, support for a model in which BCL11A might act as a repressor of γ-globin expression.

Figure 2B:
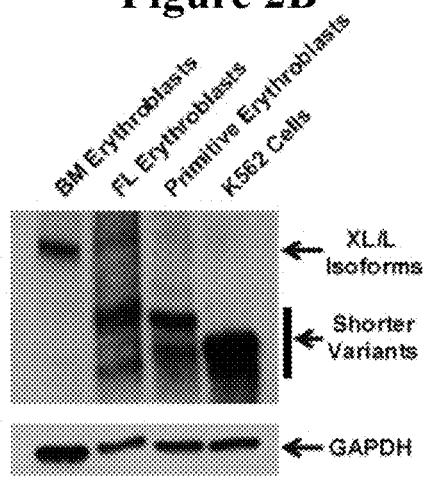
FIG. 2B show Western blots of lysates of primary human bone marrow (BM) erythroblasts, second trimester fetal liver (FL) erythroblasts, first trimester circulating primitive erythroblasts, and K562 cells. Primary human stage-matched erythroblasts were isolated by sorting for the CD235 and CD71 double-positive population. The XL and L bands migrate together here as a result of reduced separation on this blot.

Surprisingly, the embryonic erythroleukemia cell line K562 was observed to express very little, if any, of the XL and L isoforms, but instead expressed shorter variant proteins (FIG. 2B). To assess whether the difference between adult erythroblasts and K562 cells reflected developmental stage-specific control of BCL11A or the malignant nature of these cells, stage-matched, CD71+/CD235+ erythroblasts isolated from adult bone marrow were examined, second trimester fetal liver (FL), and circulating first-trimester primitive cells. FL and primitive erythroblasts, which both robustly express γ-globin (C. Peschle et al., 1985, Nature 313, 235), expressed predominantly shorter BCL11A variants (FIG. 2B) While we are currently investigating the structure of these variant proteins, the findings herein indicate that the BCL11A locus is developmentally regulated, such that full-length XL and L isoforms are expressed almost exclusively in adult stage erythroblasts. Independently, the genetic data strongly argue that the level of XL and L isoforms is influenced by sequence variants in the BCL11A gene.

BCL11A Binds the NuRD Repressor Complex, GATA-1, and FOG-1 in Erythroid Cells

To better understand the mechanism of action of BCL11A in erythroid cells, the proteins with which BCL11A interacts were characterized. First, affinity tagged versions of BCL11A in mouse erythroleukemia (MEL) cells were prepared (FIG. 3A). These cells represent a convenient model of adult-type erythroid cells that express exclusively adult globins (Papayannopoulou et. al., Cell 46:469 (1986)). The scheme used for the affinity purification in mouse erythroleukemia (MEL) cells is depicted in this diagram. Once FLAG peptide elution was performed, whole-lane mass spectrometry from acrylamide gels was done as described above. To identify specific interactions, a subtractive approach involving a simultaneous pulldown in parental Mel-BirA (MB) cells was used. The results of this subtractive screen are shown (FIG. 3B) with the number of peptides obtained in each trial listed adjacent to the identified protein. The various components of the NuRD complex are shown in blue in this table. (FIG. 3D)

No major global transcriptional changes by microarray analysis were observed upon expression of tagged versions of BCL11A in these cells (FIG. 3C). The log 2 normalized intensity of filtered probes from Affymetrix 430 2.0 arrays on the parental MB cells and a collection of four clones containing FLAG-Biotag versions of BCL11A (FBB clones) are shown in red. A linear regression is shown as a black line ($r^2$=0.9753). The microarray analysis and filtering were performed as described herein. The overall correlation coefficient ($r^2$) was 0.9753 for the log 2 normalized intensity of probes from the parental cell line compared to a collection of tagged BCL11A-expressing clones, indicating a close similarity in the transcriptional activity of these cells (with $r^2$ values of 0.9678, 0.9445, 0.9667, and 0.9736 for individual clones showing, respectively, 1, 1, 4, and 9-fold expression of tagged BCL11A compared with endogenous levels). Following affinity purification of protein complexes containing tagged BCL11A and mass spectrometric peptide sequencing, we identified numerous peptides of BCL11A, consistent with the observation that BCL11A can self-associate and these complexes appear to involve multiple isoforms (Liu et al., Mol Cancer 5, 18 (2006)) (FIG. 3B). All components of the nucleosome remodeling and histone deacetylase (NuRD) repressive complex were retrieved, suggesting a physical association between BCL11A and the complex in erythroid cells (FIG. 3B, blue), consistent with prior observations of BCL11A in B-cells and the homologue BCL11B in T-cells (Cismasiu et al., Oncogene 24:6753 (2005)). Compatible with this observed interaction, BCL11A contains an N-terminal motif that is believed in other proteins to recruit the NuRD complex (FIG. 3D) (Lauberth et. al., J. Biol. Chem. 281:23922 (2006) and Hong et al., Embo J. 24:2367 (2005)).

It was also found that the nuclear matrix protein, matrin-3 (Nakayasu et. al., Proc. Natl. Acad. Sci. U.S.A. 88:10312 (1991)), consistently co-purified with BCL11A, which may be responsible in part for the localization of BCL11A to the nuclear matrix (Liu et al., Mol. Cancer 5, 18 (2006)) (FIG. 3B). Prior work has shown that the 3 globin locus is closely associated with the nuclear matrix until later stages of erythropoeisis when high level globin gene transcription occurs (Ragoczy et. al., Genes Dev. 20:1447 (2006)). Additionally, BCL11A complexes contain peptides derived from GATA-1, the principal erythroid transcription factor (Martin, Nature 338:435 (1989)) (FIG. 3B).

This interaction was further characterized and validated. By immunoprecipitation (IP), it was confirmed that GATA-1 specifically associates with BCL11A in erythroid cells (FIG. 4A). Immunoprecipitations (IPs) were performed with M2-agarose beads. Moreover, it was found that the GATA-1 cofactor FOG-1 (Tsang et al., Cell 90:109 (1997)) also specifically associates with BCL11A and the interaction with NuRD components in erythroid cells was additionally confirmed (FIG. 4A). Prior work has shown that FOG-1 also binds to the NuRD complex (Hong et al., Embo J. 24:2367 (2005)) and these results suggest that BCL11A may synergize with this interaction in the context of specific loci.

Gel filtration fractions (every 4th fraction of 1 ml fractions is shown on the blot) from erythroid nuclear extracts are shown and blotted for BCL11A, MTA2, GATA-1, and FOG-1. On size fractionation of erythroid nuclear extracts, considerable overlap between NuRD components and BCL11A in large megadalton complexes was observed (FIG. 4B). Overlap of BCL11A with GATA-1 and FOG-1 polypeptides was less extensive (FIG. 4B). There is significant overlap between BCL11A and MTA2, with a small peak of GATA-1 and FOG-1 seen here as well. BCL11A interactions with GATA-1 (FIG. 4C) and FOG-1 (FIG. 4D) could be confirmed by exogenous expression in Cos7 cells using FLAG-tagged versions of GATA-1 or FOG-1 and V5 tagged versions of BCL11A. Using this same strategy, fragments of GATA-1 (all of which show robust expression here) could be used to map the interaction with BCL11A (FIG. 4E). Without wishing to be bound by a theory, it is possible that only a minor fraction of these factors are bound within the BCL11A and the NuRD complexes. Alternatively, in vivo association might be greater but dissociation of the components of protein complexes occurs during extract preparation and size fractionation. GATA-1 and FOG-1 immunoprecipitated with BCL11A upon exogenous expression in non-erythroid cells, which suggests that these proteins directly interact (FIGS. 4C and 4D). This approach was used to map the determinants mediating association of GATA-1 with BCL11A (FIG. 4E). It was found that BCL11A interacts with the zinc-fingers of GATA-1 (amino acids 200-338) and this interaction appears to be partially inhibited by the N-terminal region of GATA-1. The N-terminal region of GATA-1 is known to be important for normal erythropoiesis in humans (Hollanda et al., Nat. Genet. 38:807 (2006)) and is somatically mutated in an infantile myeloproliferative disorder and leukemia arising in patients with Down syndrome (Wechsler et al., Nat. Genet. 32:148 (2002); and Vyas et. al., Curr Opin Pediatr 19:9 (2007)). Together, the proteomic data indicate that BCL11A binds the NuRD complex along with GATA-1 and FOG-1 in erythroid cells. These associated factors are likely to be critical for the action of BCL11A as a transcriptional repressor in erythroid cells.

Functional Assessment of BCL11A as a Repressor of HbF Expression

Figure 5A:
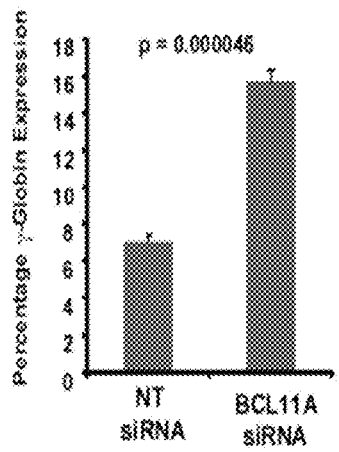
FIGS. 5A-5E demonstrate that BCL11A acts as a repressor of the γ-globin gene.

The results presented thus far provide genetic, developmental, and biochemical evidence in support of a potential role for BCL11A as repressor of γ-globin gene expression. To test this hypothesis, modulation of the level of BCL11A in primary human erythroid cells was attempted. As a cellular system in which to perform experiments, erythroid precursors from purified CD34+ human hematopoietic progenitors were expanded and differentiated. The effect of transient introduction of siRNAs that target BCL11A mRNA was examined. When siRNAs were introduced into erythroid progenitors at day 0 of differentiation, 40-45% knockdown of BCL11A mRNA levels was achieved, as assessed on day 4 of differentiation. With this knockdown, a ~2.3-fold increase in the level of γ-globin by qRT-PCR at the basophilic erythroblast stage on day 7 of differentiation was observed (FIG. 5A). With this knockdown, a 2.3-fold increase in the level of γ-globin RNA was observed (from an average of 7 to 15.7%) at the basophilic erythroblast stage on day 7 of differentiation (FIG. 5A). It was found that as these siRNAs were introduced at later time points during erythroid differentiation, lower induction of the γ-globin gene was observed (with 1.7 and 1.4-fold average γ-globin induction seen by adding siRNAs on days 1 and 2 of differentiation).

Figure 5B:
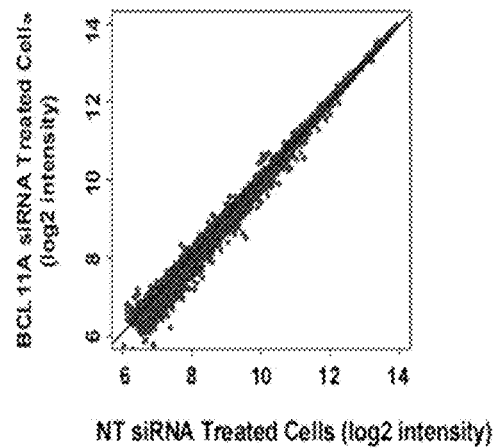

The results observed from siRNA knockdown of BCL11A could be due to a broad effect on the cellular differentiation state, which has been shown to alter γ-globin expression (Nathan et. al., Nathan and Oski's hematology of infancy and childhood. 6th, pp. 2 v. (x9) (2003) and Stamatoyannopoulos, Exp. Hematol. 33:259 (2005)), or reflect more direct action at a limited number of targets, including the γ-globin gene. To distinguish these possibilities, microarray expression profiling of the cells following knockdown of BCL11A and subsequent differentiation was performed. Microarray profiling of these cells using the Affymetrix U133 Plus 2.0 array reveals that there is close similarity in the expression profile of non-targeting and BCL11A siRNA treated cells ($r^2$=0.9901). The plot is shown with log 2 normalized probe intensities. The transcriptional profiles of genes in the quantitative range of the array (which excluded the globins) were remarkably similar between cells on day 7 after treatment with BCL11A siRNAs and non-targeting (NT) siRNAs on day 0, with an $r^2$ of 0.9901 for the log 2 normalized intensities (FIG. 5B). Additionally, the morphology of these two groups of cells was indistinguishable throughout differentiation. Together, these results suggest that knockdown of BCL11A is able to alter globin expression without causing global changes in the differentiation state of the cells.

Figure 5C:
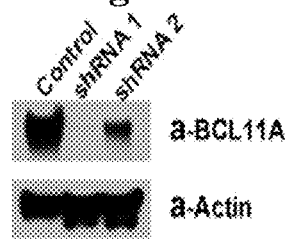
Figure 5D:
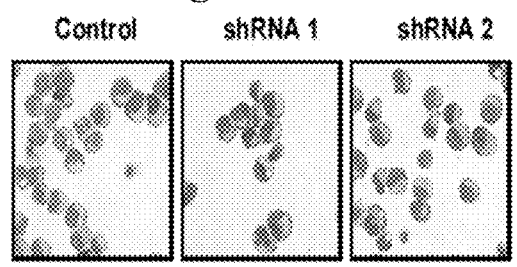

To examine the effects of more persistent reduction in BCL11A expression, lentiviral shRNA mediated knockdown of BCL11A expression with selection of transduced cells was utilized (Moffat et al., Cell 124, 1283 (2006)). Two independent shRNA constructs were chosen for this purpose. When cells were infected with the two BCL11A shRNA lentiviruses and drug selection was imposed upon the initiation of differentiation, an average of 97 and 60 percent knockdown BCL11A at the protein level by day 5 of erythroid differentiation was observed, based upon densitometry of western blots (FIG. 5C). At day 6 of differentiation (proerythroblast to basophilic erythroblast stage), the cells appear to be indistinguishable, as occurs morphologically at other stages of differentiation as well. No morphological differences between the groups of cells could be noted during the course of differentiation, suggesting that as in the case of the siRNA experiments, BCL11A knockdown was not perturbing overall erythroid differentiation (FIG. 5D).

Figure 5E:
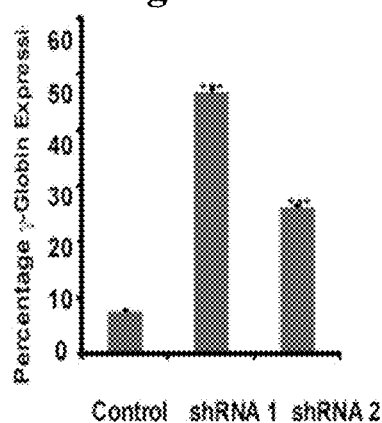
Figure 5F:
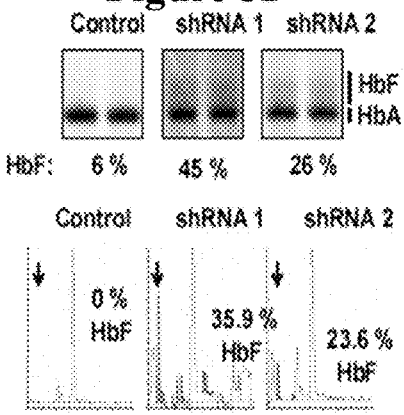
FIG. 5F shows the hemolysates prepared from cells on day 12 of differentiation show the presence of mature HbF.

The level of γ-globin at day 7 of differentiation was dramatically elevated by 6.5 and 3.5-fold (from an average of 7.4 to 46.8 and 26%) in the two sets of shRNA-mediated knockdown of BCL11A treated cells compared with the control infected cells (FIG. 5E). This robust effect is likely to be the result of both the selection for transduced cells, as well as the continuous expression of the shRNAs following viral transduction. Induction of γ-globin RNA was accompanied by corresponding levels of mature HbF, as shown by hemoglobin electrophoresis and high performance liquid chromatography (HPLC) (FIG. 5F). Hemolysates prepared from cells on day 12 of differentiation show the presence of mature HbF. This could be assessed using cellulose acetate hemoglobin electrophoresis, with the smear of HbF shown in the top panels and the average corresponding measurement from densitometry shown below these panels. This could also be more accurately quantified by hemoglobin HPLC, as shown at the bottom. The HbF peaks are labeled with an arrow in each chromatogram, with the first peak corresponding to acetylated HbF and the second unmodified HbF. The HPLC revealed that a substantial fraction of the mature hemoglobin in these cells was HbF (with an average level of 35.9 and 23.6%, compared with undetectable levels in the control). Based on the variation in the extent of knockdown of BCL11A from the siRNA and shRNA experiments and the concomitant degree of γ-globin induction seen, it appears that BCL11A may function as a molecular rheostat to regulate the silencing of the γ-globin gene.

The molecular studies of globin switching during ontogeny have served as a paradigm for the developmental control of mammalian genes. Despite extensive study, the exact molecular mechanisms underlying this process remain to be uncovered. Without wishing to be bound by theory, the results described herein suggest that BCL11A is itself a developmentally-regulated and critical modulator of this process. We have shown that BCL11A represses γ-globin gene expression in primary adult human erythroid cells. Our protein data suggest that BCL11A functions in concert with the NuRD repressor complex, GATA-1, and FOG-1. Of note, inhibitors of histone deacetylases (HDACs) appear to induce some HbF in patients with hemoglobin disorders (Perrine, Hematology Am. Soc. Hematol. Educ. Program, 38 (2005)). HDAC1 and HDAC2 are both core components of the NuRD complex and this association with BCL11A suggests that this complex may be the molecular target of these therapies. It is evident from the work on human genetics that modulation of BCL11A can elevate HbF levels and ameliorate the severity of these diseases (Lettre et al., Proc. Natl. Acad. Sci. U.S.A. (2008); Uda et al., Proc Natl Acad Sci USA 105, 1620 (2008) and Menzel et al., Nat Genet 39, 1197 (2007)). As a stage-specific component involved in repression of γ-globin expression, BCL11A emerges as a new therapeutic target for reactivation of HbF in sickle cell disease and the β-thalassemias. It is likely that the further study of BCL11A and its associated factors in globin gene regulation will lead to an improved mechanistic understanding of the fetal switch and targeted manipulation of HbF in humans.

Example 2

Materials and Methods

Experimental Animals

All experiments performed with the β-locus, K-RasG12D, BCL11A−/−, GATA1-Cre, and Mx1-Cre mice were approved by the Children's Hospital Boston animal ethics committee and the ethics committee of the Fred Hutchinson Cancer Research Center.

The wild-type β-globin locus YAC transgenic (β-YAC) mouse strains that were used in this study display a similar pattern of human globin gene expression and are representative of the various strains of transgenic mice harboring the entire human β-globin locus (Peterson, K. R. et al. 1993, Proc. Natl. Acad. Sci. U.S.A. 90:7593-7; Peterson, K. R., et al. 1998, Hum. Mol. Genet. 7:2079-88; Harju, S., et al., 2005, Mol. Cell Biol. 25:8765-78; Porcu, S. et al. 1997, Blood 90:4602-9; Gaensler, K. M., et al., 1993, Proc. Natl. Acad. Sci. U.S.A. 90:11381-5; Strouboulis, J., et al., 1992, Genes Dev. 6:1857-64). One transgenic mouse line was kindly provided by K. Peterson and was created with the insertion of a 213 kb YAC containing the entire intact human β-globin locus and has been described and characterized previously (Peterson, K. R. et al. 1993; Peterson, K. R., et al. 1998; Harju, S., et al., 2005, supra). This β-YAC line contains three intact copies of the human β-globin locus integrated at a single genomic locus. Two β-YAC lines (A20 and A85) harboring a single copy of an ~150 kb β-globin locus YAC were also used in this study and have been described previously (Porcu, S. et al. 1997, supra) (kindly provided by K. Gaensler). These transgenes were maintained in the hemizygous state. The animals were maintained on a pure C57Bl/6 background for all experiments involving adult hematopoietic analysis. A juvenile myelomonocytic leukemia-type myeloproliferative disorder was induced by crossing the Mx1-Cre line with the K-rasG12D conditional allele (Chan, I. T. et al., J. 2004, Clin. Invest. 113:528-38; Braun, B. S. et al., 2004, Proc. Natl. Acad. Sci. U.S.A. 101:597-602), along with the β-YAC transgene from K. Peterson. Congenic B6.SJL-PtprcaPep3b/BoyJ (Ptprca or CD45.1) mice were purchased from Taconic Farms or The Jackson Laboratory. Mice containing a BCL11A floxed allele (with loxP sites flanking exon 1) were created through gene targeting approaches and will be described in future work (G.C.I., S.D.M, and P.W.T., unpublished). To obtain the BCL11A null allele, these mice were crossed with GATA1-Cre mice and screened for germline deletion (Garrick, D. et al. 2006, PLoS Genet. 2:e58; Jasinski, M., et al., 2001, Blood 98:2248-55).

Adult Hematopoietic Analysis

Analyses of adult hematology, bone marrow transplants, and 5-fluorouracil (5-FU) induction were performed as described previously (Sankaran, V. G., et al., 2008, Genes Dev. 22:463-475; Walkley, C. R., et al., 2005, Nat. Cell Biol. 7:172-8). Whole PB was analyzed on a Beckman Coulter AcT (Jasinski, M., et al., 2001, supra) hematological analyzer. Recipient (CD45.1) mice were irradiated with a total of 10.5Gy γ-radiation (5Gy and 5.5Gy, 3 hours apart) on the day of transplantation. Whole BM was isolated and pooled from β-YAC mice. A total of $2 \times 10^6$ cells/mouse were retro-orbitally injected into recipients. RNA was obtained from blood using the QiaAmp Blood Mini Kit (Qiagen Inc., Valencia, Calif.) and quantitative RT-PCR (qRT-PCR) was performed as described (Sankaran, V. G., et al., 2008, supra; Sankaran, V. G. et al., 2008, Science 322:1839-42) (using the human globin gene primers listed below or previously reported murine primers (Kingsley, P. D. et al., 2006, Blood 107:1665-72). The human globin gene primers were ε-globin exon 1 forward 5'-GAGAGGCAGCAGCA-CATATC-3' (SEQ. ID. NO. 7), ε-globin exon 2 reverse 5'-CAGGGGTAAACAACGAGGAG-3' (SEQ. ID. NO. 8), γ-globin exon 2 forward 5'-TGGATGATCTCAAGGGCAC-3' (SEQ. ID. NO. 9), γ-globin exon 3 reverse 5'-TCAGTG-GTATCTGGAGGACA-3' (SEQ. ID. NO. 10), β-globin exon 1 forward 5'-CTGAGGAGAAGTCTGCCGTTA-3' (SEQ. ID. NO. 11), and β-globin exon 2 reverse 5'-AG-CATCAGGAGTGGACAGAT-3' (SEQ. ID. NO. 12). The mouse globin gene primers used were εγ globin exon 1 forward 5'-TGGCCTGTGGAGTAAGGTCAA-3' (SEQ. ID. NO. 13), εγ globin exon 2 reverse 5'-GAAGCAGAGGA-CAAGTTCCCA-3' (SEQ. ID. NO. 14), βh1 globin exon 2 forward 5'-TGGACAACCTCAAGGAGACC-3' (SEQ. ID. NO. 15), βh1 globin exon 3 reverse5'-ACCTCTGGGGT-GAATTCCTT-3' (SEQ. ID. NO. 16), βmajor/β minor globins exon 2 forward 5'-TTTAACGATGGCCTGAAT-CACTT-3' (SEQ. ID. NO. 17), and β-major/β-minor globins exon 3 reverse 5'-CAGCACAATCACGATCATATTGC-3' (SEQ. ID. NO. 18). The mouse BCL11A qRT-PCR primers were forward 5'-AACCCCAGCACTTAAGCAAA-3'(SEQ. ID. NO. 19) and reverse 5'-ACAGGT-GAGAAGGTCGTGGT-3' (SEQ. ID. NO. 20).

Developmental Hematopoietic Analysis

Embryos were obtained from timed matings, bled, and Ter119 positive cells were sorted based upon forward and side scatter similar to what has been previously described (Kingsley, P. D. et al., 2006, supra). Cells were maintained in phosphate buffered saline (PBS) with 5% fetal calf serum (FCS). Unfractionated heparin in PBS was added to this solution to a final concentration of 12.5 µg/ml. Immunohistochemistry using an anti-HbF polyclonal antibody was performed on fixed paraffin-embedded sections as described (Choi, J. W., et al., 2001, Int. J. Hematol. 74:277-80). The fetal livers of E13.5 murine embryos were dissected and a single cell suspension was created. Similarly, bone marrow cells were harvested as has been described previously from mice (Sankaran, V. G., et al., 2008, Genes Dev. 22:463-475). In both cases, the cells were labeled with Ter-1 19 and CD71, as well as 7-AAD. The Ter-119+/CD71+ populations were sorted as described previously (Sankaran, V. G., et al., 2008, supra). Stage-matched human samples were obtained and sorted as previously described (Sankaran, V. G. et al., 2008, Science 322:1839-42). These human samples were kindly provided by H. Mikkola and B. Van Handel.

Western Blot Analysis of BCL11A

Expression of BCL11A was performed using antibody 14B5 (Abcam Inc., ab19487), as described previously (Sankaran, V. G. et al., 2008, Science 322:1839-42). Expression of GAPDH was assessed as a standard using rabbit polyclonal antibody FL-335 (Santa Cruz Biotechnology Inc., sc-25778).

RNA Primary Transcript FISH

Primary transcript RNA FISH was largely performed as previously described (Wijgerde, M., et al., 1995, Nature 377:209-13; Ragoczy, T., et. al., 2006, Genes Dev. 20, 1447-57) with some modifications. Prior to hybridization, the slides were equilibrated in 50% formamide/2× SSC, pH 7.0. Single-stranded DNA probes against the introns of the murine α- and εγ- and human γ- and β-globin genes were generated by in vitro transcription of cloned intron fragments followed by reverse transcription and inclusion of DIG-11-dUTP, biotin-16-dUTP (Roche) or DNP-11-dUTP (Perkin Elmer) in the reactions as described (Bolland, D. J. et al. 2004, Nat. Immunol. 5:630-7). Labeled probes were hybridized to the cells in 50% formamide/10% dextran sulfate/2×SSC/5 mM ribonucleotide vanadate complex/0.05% BSA/0.1 mg/ml Cot-1 DNA/1 g/µl *E. coli* tRNA. The probes were heat denatured at 80° C. for 5 minutes, preannealed at 37° C., and then hybridized overnight at 37° C. in a humid chamber. Slides were washed in 50% formamide/2×SSC, pH 7 at 37° C., rinsed in 2×SSC and blocked in 145 mM NaCl/0.1M Tris pH 7.5/2% BSA/2 mM ribonucleotide vanadate complex. Primary transcript foci were detected by indirect immunofluorescence with Cy3-, Alexa Fluor 488- and 647-conjugated antibodies including one or two layers of signal amplification, as described (Trimborn, T., et al., 1999, Genes Dev. 13, 112-24).

FISH Image Acquisition and Analysis

Image stacks (Z sections spaced 0.25 m apart) were captured on an Olympus IX71 microscope (Olympus objective 100×/1.40, UPLS Apo) equipped with a cooled CCD camera using Deltavision SoftWorx software (Applied Precision). The presence of the globin gene primary transcripts was determined in 2D projections of the Z stacks using Photoshop (Adobe). About 100-200 nuclei were analyzed for each probe set and maturation stage.

Chromatin Immunoprecipitation (ChIP) of Primary Erythroid Cells

Human CD34-derived erythroid progenitors were harvested on day 5 of differentiation (proerythroblast stage). The cells were fixed using a 1% final concentration of formaldehyde and cross-linking was allowed to proceed for 10 minutes. Glycine to a final concentration of 125 mM was then introduced to stop the cross-linking. Cells were washed twice in PBS and cell pellets were stored at −80° C. Typically ~15-20×$10^6$ cells were used per ChIP reaction. The ChIP assays were performed in a similar manner to what has previously been described in J. Kim, et al., 2008, Cell 132:1049. The sonication buffer was modified with the use of 0.5% SDS, instead of 0.1%. The sonication procedure was modified with the use of 4 to 6 pulses of 30 seconds, each involving constant sonication. This exact procedure typically produces fragments in the range of 300-1000 base pairs with this procedure. The following antibodies were used for the ChIP procedure: BCL11A [14B5] (Abcam, ab19487), BCL11A [15E3AC11] (Abcam, ab18688), BCL11A (Novus Biologicals, Inc. NB600-261), and Rabbit IgG (Upstate, 12-370). Similar results were obtained with all BCL11A antibodies in all the regions tested.

The ChIP samples were analyzed by real-time quantitative PCR (BioRad). All primers were tested for PCR efficiency as recommended by the manufacturer (BioRad). A standard curve was prepared for each set of primers using serial titration of the input DNA. The relative amount of precipitated chromatin (percent of input) was calculated from primer-specific standard curves using the iCycler Data Analysis Software. The specific primers were designed to amplify sequences at the HS3; HBG1 promoter region; HBG1 downstream region (+3 kb); HBD upstream region (−1 kb); and HBB promoter region of the human β-globin locus. Additionally, a degenerate primer set that bound to the promoters of both HBG2 and HBG1 was used and showed similar results to the HBG1 promoter primer set (with no enrichment detected).

Results

The contribution of changes in cis-regulatory elements or trans-acting factors to interspecies differences in gene expression is not well understood. The mammalian β-globin loci have served as a paradigm for gene regulation during development. Transgenic mice harboring the human β-globin locus, consisting of the linked embryonic (ε), fetal (γ) and adult (β) genes, have been used as a model system to study the temporal switch from fetal to adult hemoglobin, as occurs in humans. The inventors show that the human γ-globin genes in these mice behave as murine embryonic globin genes, revealing a limitation of the model and demonstrating that critical differences in the trans-acting milieu have arisen during mammalian evolution. The inventors show that the expression of BCL11A, a repressor of human γ-globin expression identified through genome-wide association studies, differs between mouse and human. Developmental silencing of the mouse embryonic globin and human γ-globin genes fails to occur in mice in the absence of BCL11A. Thus, BCL11A is a critical mediator of species-divergent globin switching. By comparing the ontogeny of β-globin gene regulation in mice and humans, the inventors have shown that alterations in expression of a trans-acting factor constitute a critical driver of gene expression changes during evolution.

Figure 10:
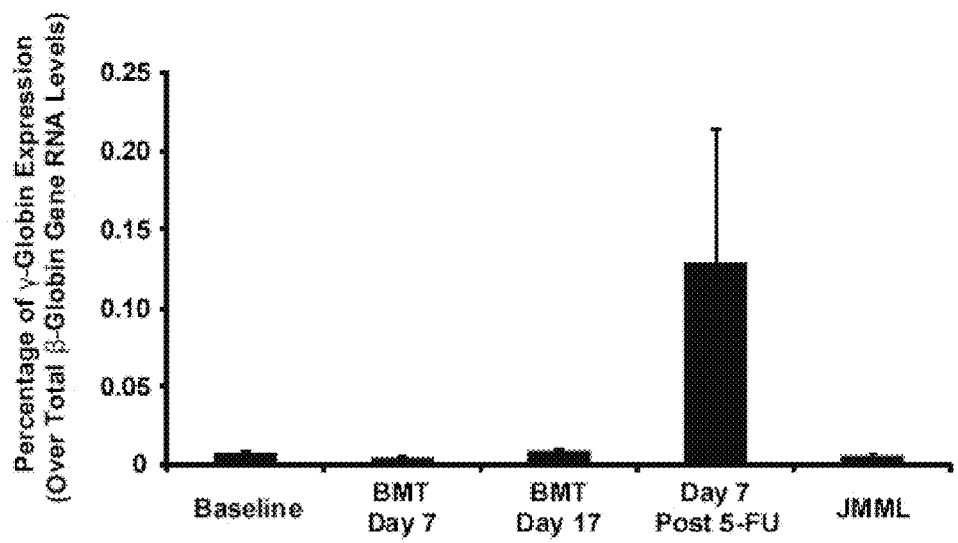
FIG. 10 shows the inability to recapitulate stress responses in adult β-YAC mice. Adult β-locus mice were induced with a variety of γ-globin stimulating responses.

The extent to which changes in cis-regulatory elements or the trans-acting environment account for differences in gene expression in closely related species is the subject of debate (Carroll, S. B., 2008, Cell 134:25-36; Hoekstra, H. E. and Coyne, J. A., 2007, Evolution 61:995-1016). Some studies suggest that changes in cis-regulatory elements are largely responsible for many interspecies differences in gene expression (Wallace, H. A. et al., 2007, Cell 128:197-209; Wilson, M. D. et al., 2008, Science 322:434-8). The contribution of alterations in the trans-acting milieu is less established. With their temporal switches of globin expression, mammalian β-globin loci serve as a paradigm for developmental gene regulation (McGrath, K. & Palis, J., 2008, Curr. Top. Dev. Biol. 82:1-22). To study the regulation of human cis-elements in a mouse trans-acting environment, the inventors employed human β-globin locus transgenic mice (β-locus mice). The regulation of the human β-globin locus has been widely studied using such mouse models (Wijgerde, M., et al., 1995, Nature 377:209-13; Peterson, K. R., et al., 1998, Hum. Mol. Genet. 7:2079-88; Porcu, S. et al., 1997, Blood 90:4602-9). It is generally accepted that these mice provide a valid system for evaluating human developmental globin gene regulation, though some differences have been noted between humans and these mice. For example, the onset of γ-globin expression occurs during the embryonic, yolk sac stage of erythropoiesis in the mouse, while high-level expression of this gene occurs during the fetal liver stage in man. Moreover, the switch from γ-globin to adult β-globin occurs during early fetal liver erythropoiesis in these mice (Wijgerde, M., et al., 1995; Peterson, K. R., et al., 1998, Porcu, S. et al., 1997, supra), whereas it occurs around the time of birth in humans (Peschle, C. et al., 1985, Nature 313, 235-8). In addition, differences have been noted in the capacity of these mice to respond to fetal hemoglobin (HbF) eliciting responses that are active in humans (Sloane-Stanley, J., 2006, Br. J. Haematol. 135:735-7; Pace, B., et al., 1994, Blood 84:4344-53). The inventors began by evaluating whether these mice respond to stimuli that consistently increase the level of HbF in humans (Papayannopoulou, T., et al., 1984, Science 224:617-9). The inventors found that these mice have much lower basal levels of γ-globin expression than adult humans and fail to respond to stimuli that result in elevated levels of HbF in humans (FIG. 10). The graph shows, respectively, the baseline measurement in adult mice (n=10), bone marrow transplants with 2X106 donor (β-locus mice) marrow cells (Alter, B. P., et al., 1976, Blood 48:843-53) (n=10) at days 10 and 17 post-transplant, 5-FU treatment when cytopenias are at their nadir on day 7 (n=10), and a juvenile myelomonocytic leukemia (JMML)-type of myeloproliferative disorder from activation of K-ras (Braun, B. S. et al. 2004, Proc. Natl. Acad. Sci. U.S.A. 101:597-602; Chan, I. T. et al. 2004, J. Clin. Invest 0.113:528-38) (n=3). Data is plotted as percentage of γ-globin over total human β-like globin gene levels calculated based upon qRT-PCR results. Results are shown as the mean±standard deviation of the mean. Of note, the baseline level of γ-globin is 50 to 100-fold lower than in human adults (Oneal, P. A. et al. 2006, Blood 108:2081-6; Nathan, D. G., et al., 2003, in Hematology of infancy and childhood, 2 v. (xiv, 1864, xli p.) (Saunders, Philadelphia, Pa.,). Also, in a model of juvenile myelomonocytic leukemia created in these mice, no elevation in γ-globin levels was observed, in contrast to the high levels of γ-globin seen in humans with this syndrome (Weatherall, D. J. et al., 1975, Nature 257:710-2).

Human Fetal γ-Globin Genes Behave as Embryonic Genes in the Mouse

To pursue the underlying basis of these species differences, the inventors reassessed the ontogeny of human γ-globin expression during mouse development. The inventors first isolated circulating blood from embryos at a time when γ-globin expression is observed (E13.5) (Wijgerde, M., et al., 1995, Nature 377:209-13; Peterson, K. R., et al., 1998, Hum. Mol. Genet. 7:2079-88; Porcu, S. et al., 1997, Blood 90:4602-9). Using differences in cell size that permit separation of circulating primitive and definitive lineage cells using flow cytometry (Kingsley, P. D. et al., 2006, Blood, 107:1665-72; Fraser, S. T., et al., 2007, Blood, 109:343-52), the inventors enriched the erythroid cells in blood from embryonic day 13.5 (E1 3.5) β-locus mice (FIG.

Figure 6A:
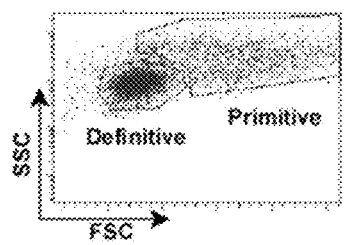
FIGS. 6A-6H show that human γ-globin is primarily expressed in primitive erythroid cells of β-locus mice.
Figure 6B:
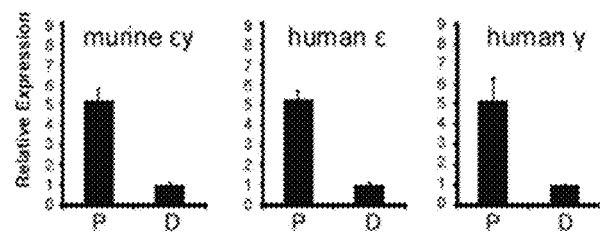

6A). As anticipated, expression of the mouse embryonic gene εγ globin, a gene confined to the primitive erythroid lineage along with mouse βh1 globin (Kingsley, P. D. et al., 2006, Blood, 107:1665-72; Fraser, S. T., et al., 2007, Blood, 109:343-52), was enriched (approximately 5-fold) in the primitive population relative to the definitive population (FIG. 6B). Consistent with this distribution, human embryonic ε-gobin transcripts were similarly enriched in the primitive population (FIG. 6B). Surprisingly, there was no difference observed between the relative enrichment of the embryonic genes and the degree of enrichment of human γ-globin transcripts in the primitive erythroid population compared to the definitive cells (FIG. 6B). This finding indicates that the human γ-gobin genes are not robustly expressed in early definitive erythroid cells in β-locus mice.

Figure 6C:
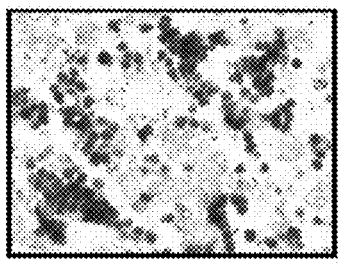
Figure 6D:
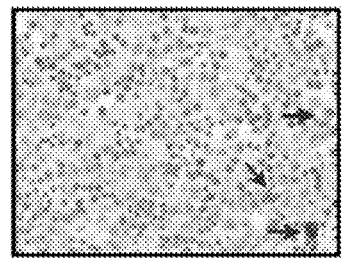
Figure 6E:
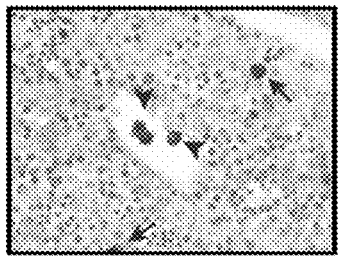
Figure 6F:
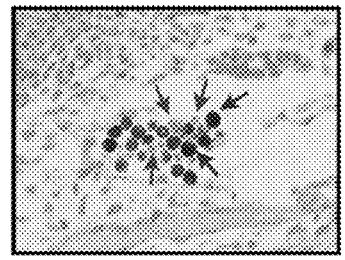
Figure 6G:
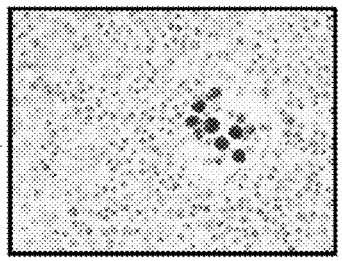
Figure 6H:
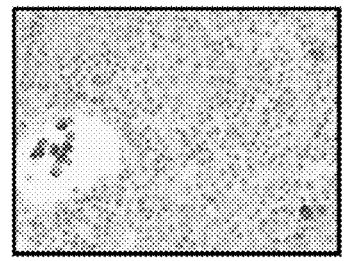

The inventors then used immunohistochemistry (IHC) of γ-globin in E13.5 embryos to examine its cellular distribution. IHC of human fetal liver (FL) revealed positive labeling of all erythroblasts (FIG. 6C). In contrast, the majority of erythroblasts present in the murine FL of β-locus mice failed to stain for γ-globin. The inventors observed occasional large nucleated, megaloblastic cells in FL positive for γ-globin (FIGS. 6D and 6E). Morphologically these cells resemble primitive cells that continue to circulate in substantial numbers during this period of gestation (McGrath, K. & Palis, J., 2008, Curr. Top. Dev. Biol. 82:1-22). Consistent with this interpretation, the numerous γ-globin positive cells seen in the circulation were all megaloblastic primitive cells, whereas enucleate, smaller definitive cells were uniformly negative (FIGS. 6E and 6F). To generalize these findings, the inventors performed similar immunohistochemical staining in other independently-derived lines of β-locus mice (FIGS. 6G and 6H) (Porcu, S. et al., 1997, Blood 90:4602-9). In all lines, γ-globin expression (as indicated by positive IHC) was confined to circulating megaloblastic cells that were infrequent in FL parenchyma. As similar observations have been made in independently derived β-locus mice, the inventors findings demonstrate a characteristic feature of β-locus mice.

Figure 7A:
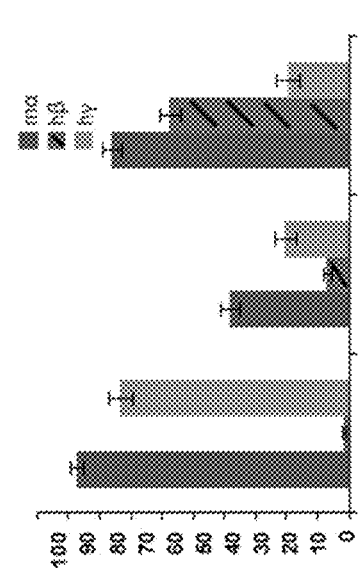
FIGS. 7A-7D show PT-FISH analyses revealing that γ-globin expression parallels the murine embryonic globins in primitive erythroid cells. Two independent lines of transgenic YAC mice, A85 (FIGS. 7A and 7C) and A20 (FIGS. 7B and 7D) were analysed using four color primary transcript RNA fluorescence in situ hybridization (PT-FISH). For the first set of experiments, probes were made to target murine α-globin (mα), human β-globin (hβ), and human γ-globin (hγ). Additionally, DAPI was used to identify nuclei of cells.

Single Cell Analysis Confirms the Divergent Behavior of Human β-Globin Loci in Mice To gain additional insight at the single cell level, the inventors employed primary transcript RNA fluorescence in situ hybridization (PT-FISH) to examine the relative expression of the endogenous mouse and human globin genes at different stages of ontogeny (Ragoczy, T., et al., 2006, Genes Dev. 20:1447-57; Trimborn, T., 1999, Genes Dev. 13:112-24). First, the inventors examined the relative expression of human γ- and β-globin (with murine α-globin as a control) in E1 1.5 primitive erythroid cells from two independent transgenic lines (A20 and A85). Consistent with prior analyses demonstrating high-level expression of γ-globin at the primitive erythroid stage in β-locus mice, the inventors noted relatively high expression of γ-globin by PT-FISH, with low or absent expression of human β-globin (FIGS. 7A and 2B). Among circulating primitive cells from a later stage of development (E13.5) a similar pattern was observed, although more human β-globin expression was seen and an overall reduction in the percentage of cells with a PT-FISH signal (using the murine α-globin control) was noted, with only a fraction of cells (~⅓) showing transcriptionally active loci at a single time point (FIGS. 7A and 7B). Examples of the cells used in this analysis are shown (data not shown). An interesting observation made with concomitant PT-FISH analysis of human γ- and β-globin is the extent of cotranscription, which represents the concomitant presence of two primary transcript signals within the same gene locus (data not shown).

Analysis of Cotranscription by Primary Transcript Fluorescence In Situ Hybridization (PT-FISH) Analysis Cotranscription is defined as the simultaneous presence of two primary transcript signals from the same gene locus in a single cell. High frequency of cotranscription is seen in this analysis, particularly at stages when little of the mature γ-globin gene is expressed. In the peripheral blood cells (circulating primitive cells) from embryonic day 13.5 (E13.5), 19 and 21% (in the A85 and A20 lines, respectively) of cells expressing γ-globin show cotranscription of β-globin (data not shown). In the fetal liver cells from E13.5, this degree of overlap increases dramatically, with 52 and 55% of cells expressing γ-globin showing cotranscription of β-globin (data not shown). The nature of such cotranscription is unclear. It has previously been ascribed to a rapid flip-flop mechanism of the locus control region (LCR) with the downstream globin genes (Wijgerde, M., et al., 1995, Nature 377:209-13). The results suggest that primary transcripts may be generated by cotranscription even in the absence of robust transcription (as indicated for γ-globin in E13.5 FL cells). Since PT-FISH is limited to a single snap-shot of transcription, it is unclear whether the rate of transcription at cotranscribed loci is comparable. These findings suggest that the rate and/or efficiency at these concomitantly transcribed loci likely vary and therefore the presence of primary transcripts, particularly in the context of cotranscription, may not indicate efficient production of mature transcripts.

Figure 7C:
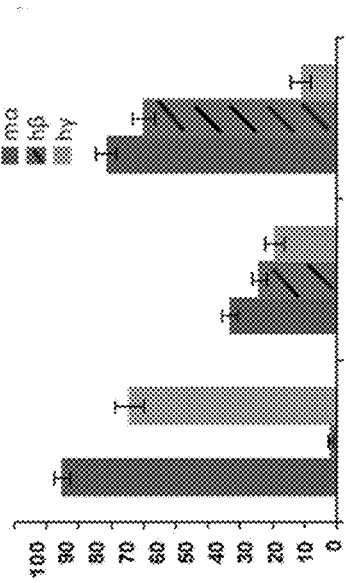
Figure 7B:
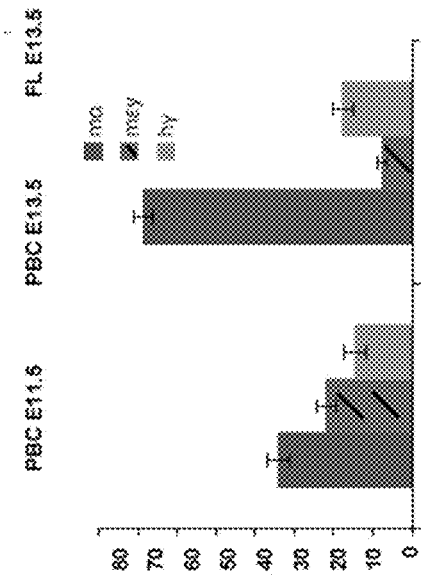
Figure 7D:
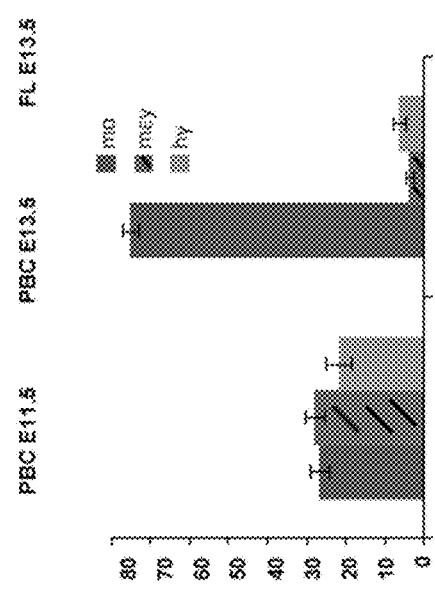

Comparison of mouse embryonic εγ-globin with γ-globin revealed similar expression of the mouse embryonic gene with human g-globin in circulating primitive cells from E13.5 (FIGS. 7C and 7D). This finding indicates that expression of the human γ-globin genes parallels that of mouse embryonic β-like genes in the mouse trans-acting environment. FL cells from E13.5 were analyzed in a similar manner, by examining the expression of mouse εγ and human γ-globin by PT-FISH in these cells. Only a low percentage of cells showed staining for either εγ or γ-globin (FIGS. 7C and 7D), compared with robust transcription of human β-globin at the same stage (FIGS. 7A and 7B). Consistent with prior developmental analyses in mice (Kingsley, P. D. et al., 2006, Blood, 107:1665-72; Trimborn, T., 1999, Genes Dev. 13:112-24), cells positive for mouse εγ represent circulating primitive cells present within the mouse fetal liver. The cells that are positive for human γ-globin expression are also likely to be primitive erythroid cells, and it is important to recognize that in these cells only a fraction (~⅓) of loci are active at any single time point, thereby limiting the degree of concomitant expression seen. Of note, 45 and 54% (in the A85 and A20 lines, respectively) of the primitive cells from E13.5 (PBC) with γ-globin transcript showed expression of εγ globin, supporting the notion that γ-globin is treated as an embryonic gene in the mouse trans-acting environment. Interestingly, an early analysis of very low expressing transgenes lacking critical locus region regulatory sequences had suggested that γ-globin indeed behaved as an embryonic gene, as we have shown for mice containing the entire robustly expressed human β-locus (Chada, K., et al., 1986, Nature 319:685-9).

Figure 8A:
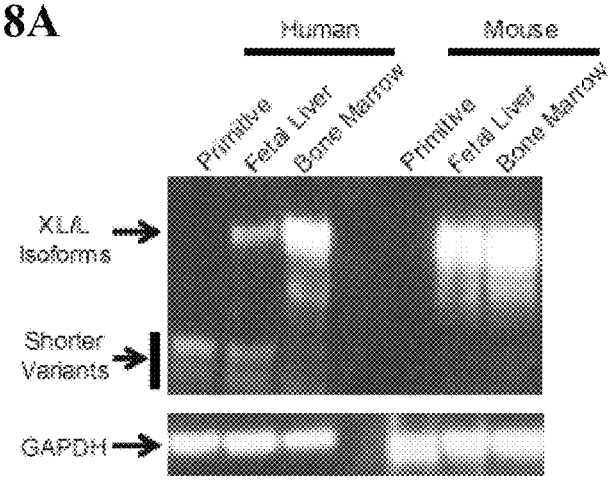
FIGS. 8A-8B show that BCL11A expression varies between humans and mice, indicating a model for trans-acting variation in β-globin gene expression.
Figure 8B:
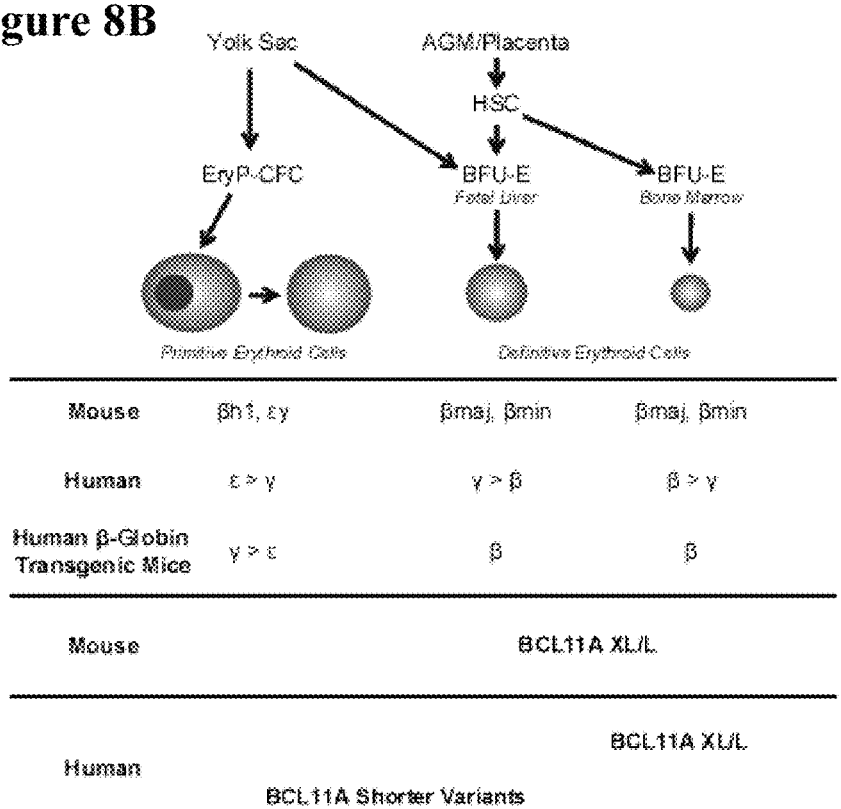
Figure 11:
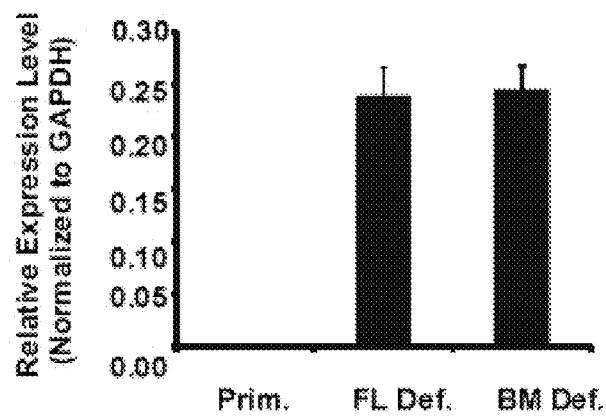
FIG. 11 shows that BCL11A RNA is expressed in mouse definitive cells, but not primitive cells.

BCL11A Restricts Mouse Embryonic β-Like Globin Expression to the Primitive Lineage From these results it was concluded that the homologous mouse erythroid trans-acting environment differs from that of the human, presumably with respect to the composition or regulation of critical transcriptional regulators. It has recently been shown that the gene BCL11A, which harbors genetic variants that affect HbF levels in humans (Uda, M. et al., 2008, Proc. Natl. Acad. Sci. U.S.A. 105:1620-5; Lettre, G. et al., 2008, Proc. Natl. Acad. Sci. U.S.A. 105: 11869-74; Menzel, S. et al., 2007, Nat. Genet. 39:1197-9; Sedgewick, A. E. et al., 2008, Blood Cells Mol. Dis. 41:255-8), encodes a developmental stage-specific repressor of the human γ-globin genes (Sankaran, V. G. et al., 2008, Science 322:1839-42). The prior findings were confined to an analysis of human erythroid cells, where we found that forms of full-length BCL11A were expressed robustly in adult bone marrow erythroblasts, at substantially lower levels in FL, and absent within primitive erythroblasts. Moreover, shorter variant forms of BCL11A are expressed in human primitive and FL erythroblasts, both of which express γ-globin. To investigate potential species differences in BCL11A protein expression, we examined stage-matched, FACS-sorted populations of mouse and human erythroid cells. Remarkably, comparison of BCL11A expression in mouse and human samples reveal striking differences (FIG. 8A, FIG. 11). The expression of BCL11A RNA measured by qRT-PCR in sorted stage-matched cell populations (sorted for CD71 and Ter-119) from different developmental stages in mice demonstrates that BCL11A RNA is expressed at similar levels in all definitive populations of murine cells, but was absent or expressed at markedly reduced levels in primitive cells (normalized to GAPDH). First, BCL11A protein and RNA transcripts are absent in primitive erythroid cells of mice. Second, full-length forms of BCL1 1A are expressed at similar levels in definitive erythroid cells of both mouse FL and bone marrow, whereas no shorter variant forms could be identified in mice (FIG. 8A). Additionally, short variant forms are present at these earlier developmental stages. All human cells were sorted for CD235 and CD71 expression. In contrast, in murine cells, full-length BCL1 1A protein expression is evident in all definitive progenitor populations, including sorted stage-matched E13.5 fetal liver and bone marrow erythroid cells (all populations were sorted for Ter119+/CD71+). No expression of BCL11A within murine primitive cell populations was detected. These results highlight important interspecies differences that could potentially play a role in mediating divergent globin gene regulation. A model based upon our findings of the developmental expression of the β-like globin genes in humans, mice, and β-locus mice is shown, along with a summary of BCL11A expression in these two species (FIG. 8B).

Figure 12A:
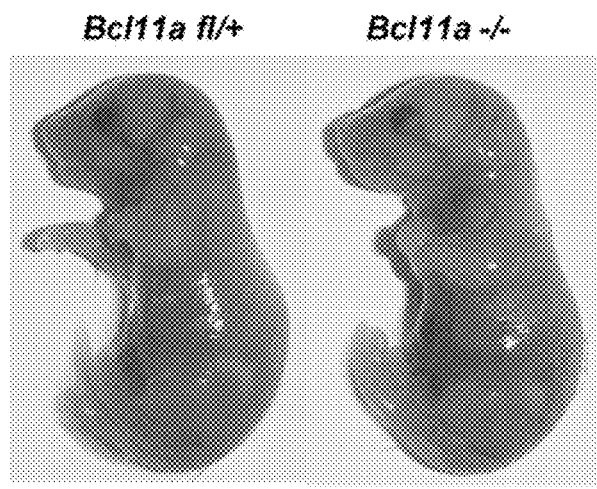
FIGS. 12A and 12B show that BCL11A−/− mice are morphologically normal and completely lack BCL1 1A protein expression in the fetal liver.
Figure 12B:
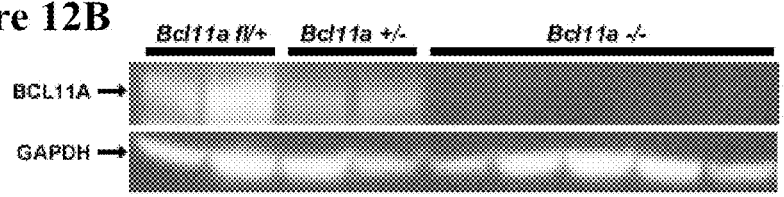
Figure 13:
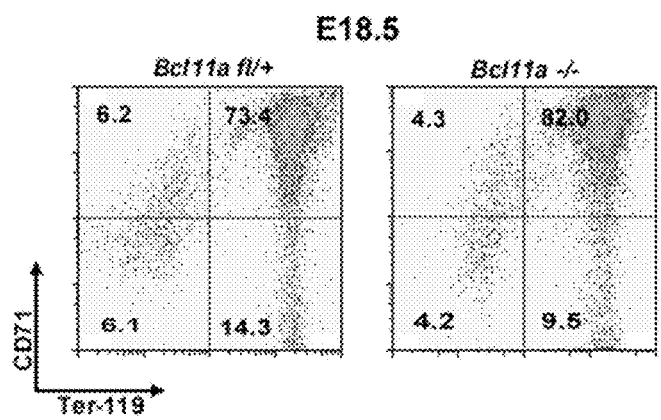
FIG. 13 shows that BCL11A−/− mice have normal phenotypic erythropoiesis at E18.5. Erythroid maturation was assessed using the markers CD71 and Ter-1 19 in the fetal livers of E18.5 animals (Sankaran, V. G., et al., 2008, Genes Dev 22, 463-475). The mean values in each quadrant are shown (n=9 for the controls and 7 for the null animals).
Figure 14:
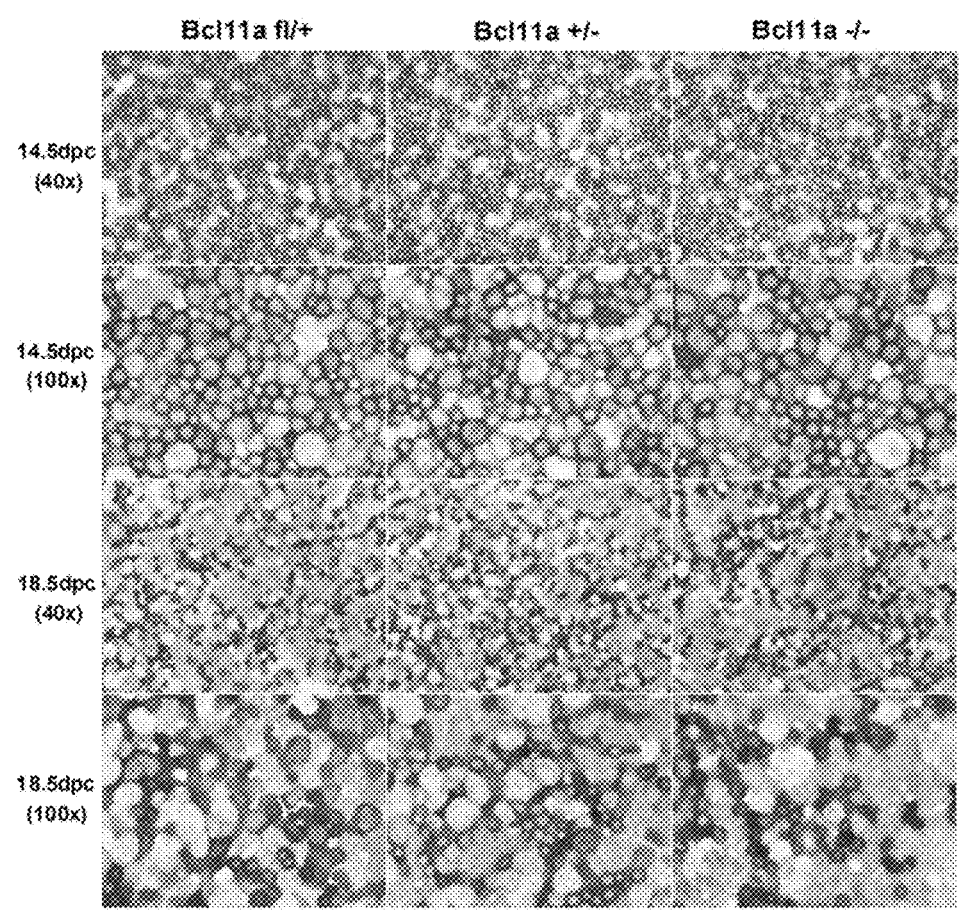
FIG. 14 shows that BCL11A−/− mice have normal erythroid morphology. Example cytospin preparations from single cell suspensions of the fetal liver stained with May-Grünwald-Giemsa stain are shown from E14.5 and E18.5. All images were viewed with a 10× objective and with the lens magnifications shown.
Figure 15A:
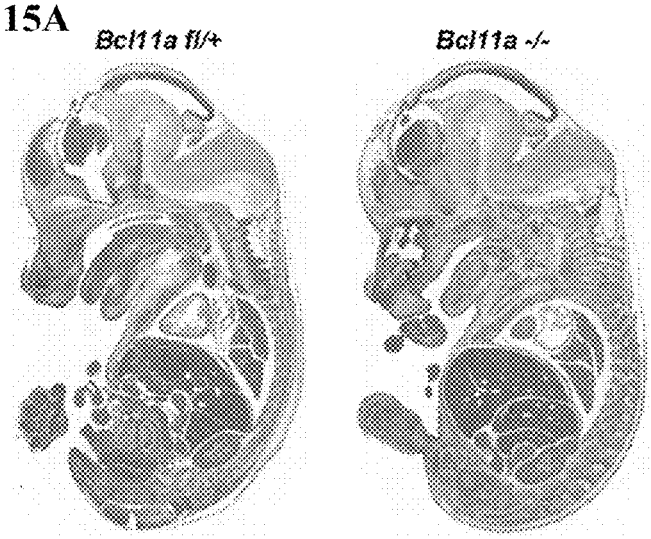
FIGS. 15A and 15B are histological analyses of fetal livers from BCL1 1A−/− mice revealing normal gross histology and morphological erythropoiesis.
Figure 15B:
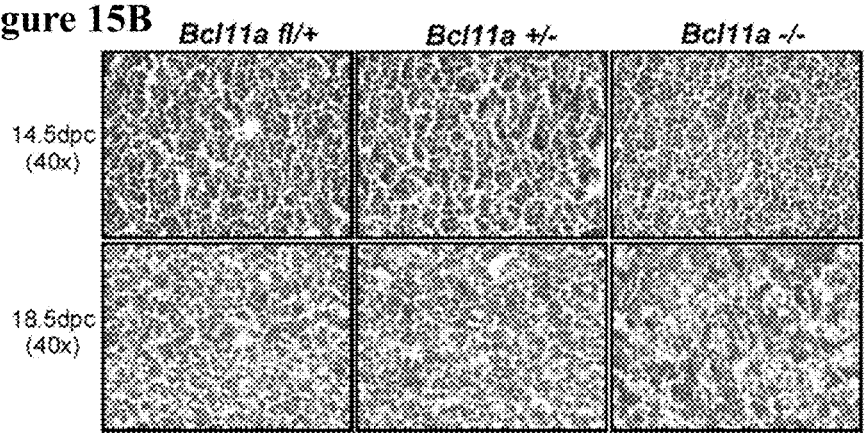
Figure 16A:
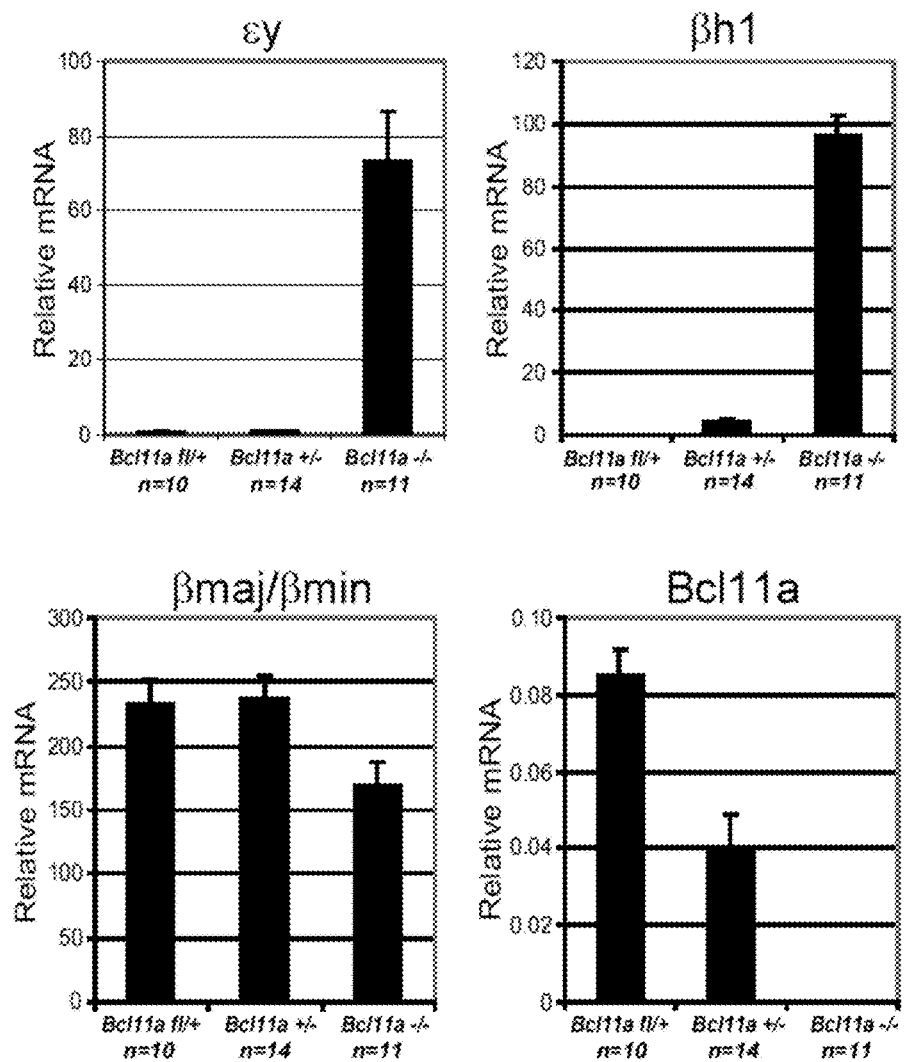
FIGS. 16A and 16B show that BCL1 1A−/− have an upregulation of embryonic globins in the fetal liver.
Figure 16B:
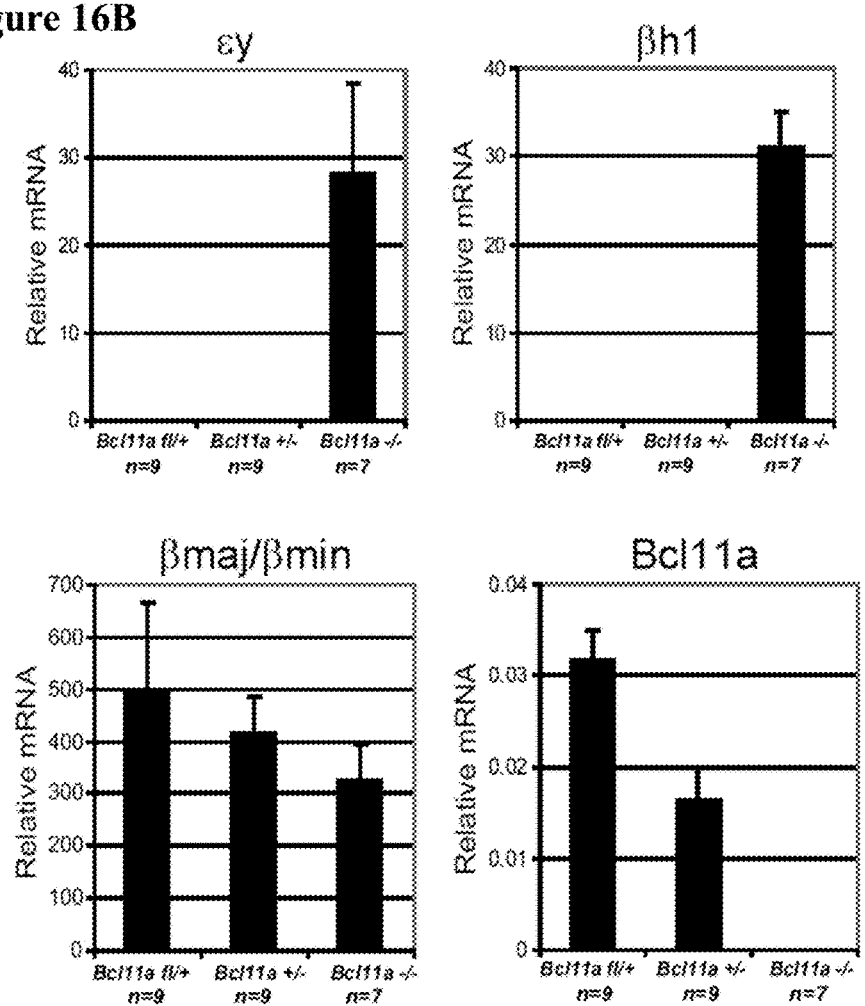
Figure 17:
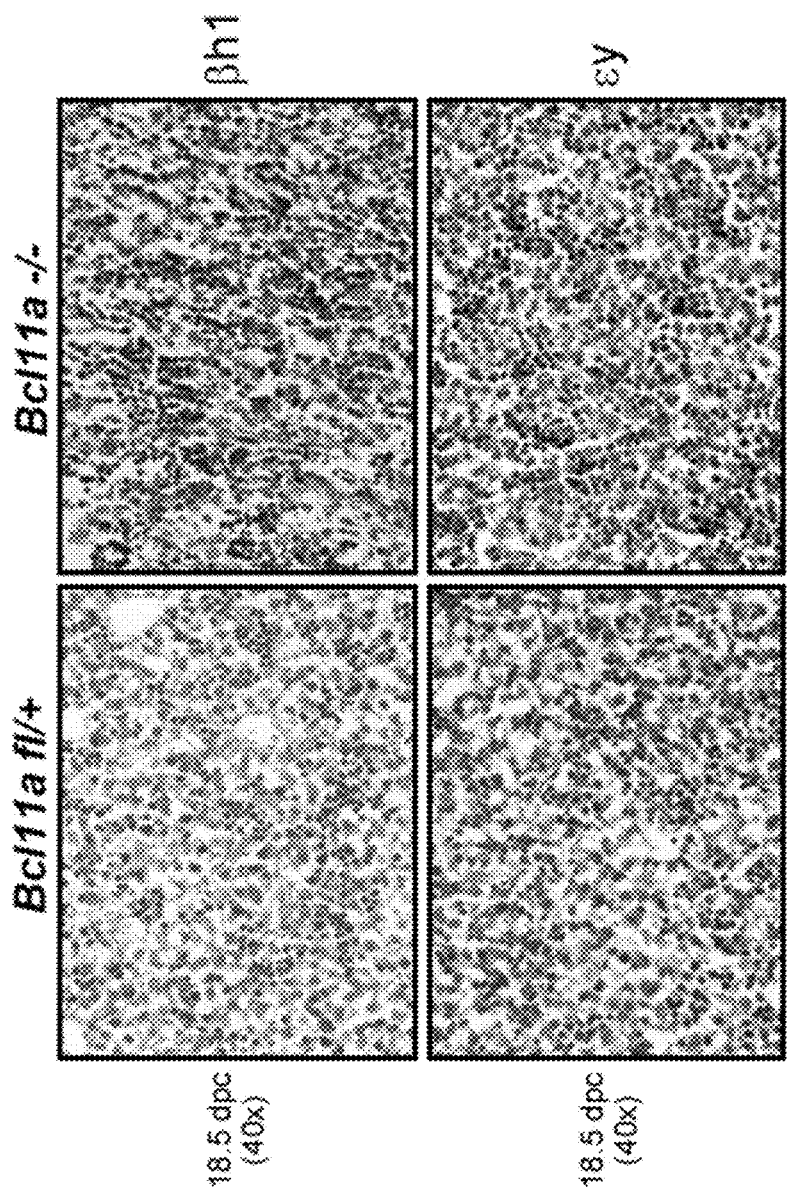
FIG. 17 is the immunohistochemistry of BCL1 1A−/− mice showing an upregulation of embryonic globins in the fetal liver. Immunohistochemistry was performed on E18.5 FLs from BCL11A fl/+ and −/− animals for the embryonic globin βh1. Representative sections at 40× magnification with a 10× objective lens are shown. Similar IHC staining was performed for εγ globin as labeled in the figure.

The inventors demonstrated that expression of the human γ-globin genes strictly parallels that of the mouse embryonic genes, εγ and βh1, in the context of the mouse trans-acting environment. Moreover, the pattern of BCL1 1A expression suggests a role throughout definitive erythropoiesis in mice, as opposed to its predominant role after birth in humans. Thus it was hypothesize that changes in expression of BCL11A may be responsible, at least in part, for the observed interspecies divergent expression of β-like globin genes. To test directly a potential role for BCL11A in silencing the endogenous embryonic genes in the definitive erythroid lineage, BCL11A knockout mice was examined. As described previously (Liu, P. et al. 2003, Nat. Immunol. 4:525-32), BCL11A−/− mice die in the perinatal period from unknown causes. BCL11A−/− mice at E14.5 and E18.5 during gestation were examined when robust definitive erythropoiesis is taking place within the FL (FIG. 12). By phenotypic and morphologic approaches (Sankaran, V. G. et al., 2008, Genes Dev. 22:463-475; Zhang, J., et al., 2003, Blood, 102:3938-46), erythropoiesis appeared ostensibly normal within these embryos (FIG. 9A, FIGS. 13-15). Then, the expression of the mouse globin genes was assessed. In strong support of the inventors' hypothesis, it was observed that silencing of expression of mouse embryonic globin genes fails to occur in E14.5 and E18.5 FL erythroid cells (FIG. 9B-E, FIG. 16). Restriction of embryonic globin expression to the primitive lineage is lost. Expression of the εγ and βh1 globin genes was up-regulated by 70 and 350-fold, respectively, at E14.5 (FIG. 9B). Together these embryonic globin genes account for 50 percent of the total β-like globin genes at this stage, compared with 0.4 percent in the controls. At E18.5, while the contribution of their transcripts to total β-like globin transcripts was somewhat reduced, εγ and βh1 globin transcripts were 2600 and 7600-fold elevated compared to controls (FIG. 9C). To determine the cellular distribution of the mouse embryonic globins, immunohistochemistry was performed. Using this approach, we found that βh1 and εγ globins were robustly expressed in definitive erythroid cells (FIGS. 9D and 9E, FIG. 17), whereas normally these embryonic globins are confined to the primitive erythroid lineage (McGrath, K. & Palis, J., 2008, Curr. Top. Dev. Biol. 82:1-22) (FIG. 8B).

Silencing of Human γ-Globin Expression Depends on BCL11A

We then examined the consequence of BCL1 1A loss on regulation of human globin genes in the β-locus mice. By introducing the β-locus transgene into the knockout environment, we found that in the absence of BCL1 1A developmental silencing of the γ-globin genes is markedly impaired in the definitive erythroid lineage (FIG. 9F, FIG. 18). In BCL11A−/−, +/−, and littermate control mice γ-globin RNA comprised 76, 20, and 0.24 percent of total β-like globin gene RNA at E18.5, respectively (FIG. 9F, FIG. 18). Relaxation of γ-globin gene silencing in BCL11A+/− heterozygotes is consistent with the genetic association of BCL1 1A and HbF levels and extends our prior observations using knockdown approaches in human cells (Sankaran, V. G. et al., 2008, Science 322:1839-42) that together point to BCL11A as a quantitative regulator of γ-globin expression. The failure of γ-globin gene silencing in the face of otherwise ostensibly normal erythropoiesis provides compelling evidence that BCL11A is a major regulator of the globin switches in mouse and human ontogeny.

Figure 19:
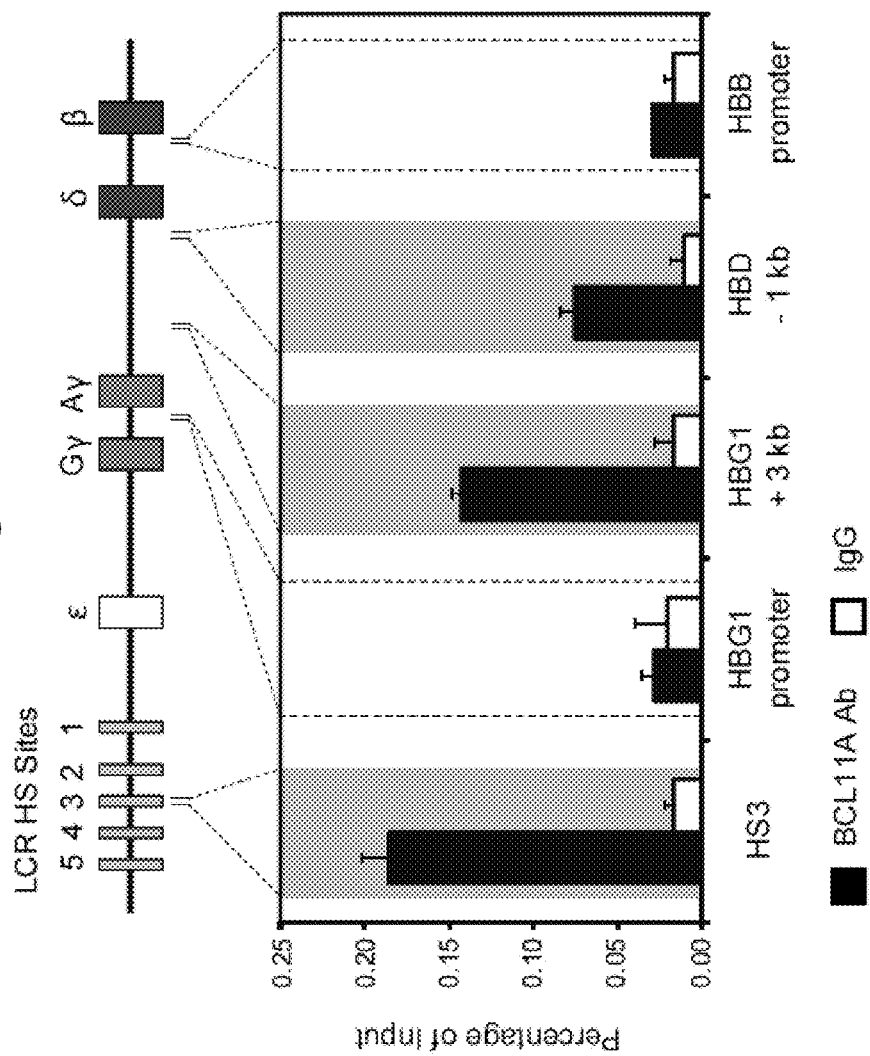
FIG. 19 show that BCL11A occupies discrete regions in the human β-globin locus in adult erythroid progenitors. The human β-globin locus is depicted at the top with regions showing significant binding shaded in gray in the histogram plot below. The results are depicted as the mean with the standard deviation as error bars (n=3 per group).

In principle, BCL11A might influence globin gene expression either directly by interacting with cis-regulatory elements within the β-globin cluster or indirectly by affecting cell cycle or other pathways that ultimately impinge on HbF expression. To discriminate these possibilities, chromatin immunoprecipitation (ChIP) was utilized to study primary human erythroid progenitors. Occupancy of neither the γ- or β-globin proximal promoters was detected. Rather, robust binding in several other regions of the β-globin cluster was observed (FIG. 19). These include the third hypersensitivity site (HS3) of the locus control region (LCR) (P. A. Navas et al., 1998, Mol. Cell. Biol. 18:4188), the region of the high HbF-associated Corfu deletion upstream of the δ-globin gene (A. Bank, 2006, Blood 107:435), and another region downstream of the Aγ-globin gene that is commonly deleted in certain forms of hereditary persistence of fetal hemoglobin (A. Bank, 2006, Blood 107:435). Of particular note, all of these cis-elements have been suggested to play a role in γ-globin silencing. The present results strongly argue that BCL11A acts within the β-globin cluster. Shorter BCL11A variants present in cells that actively express γ-globin may participate in others aspects of transcriptional regulation within the β-globin cluster. Thus BCL11A, at different levels and in its variant forms, reconfigures the β-globin locus at different development stages.

CONCLUSION

Taken together, the findings here demonstrate how changes in expression of a single transacting factor over the course of evolution may lead to altered developmental gene expression. Shown herein is that cis-elements within the human β-globin locus are insufficient to recapitulate proper developmental regulation in a mouse context. Previously it has been postulated that the evolution of β-like globin gene expression is largely mediated through changes in cis-elements (Johnson, R. M. et al. 2006, Proc. Natl. Acad. Sci., U.S.A. 103:3186-91). The findings herein argue persuasively that changes in transacting factors may exert striking effects on gene switching during development. BCL11A serves to silence the embryonic genes in mouse definitive erythroid cells, in contrast to its role in humans where it acts to silence γ-globin expression after birth. Moreover, we show that BCL11A is a powerful regulator of the species divergent globin switches by demonstrating that the γ-globin gene escapes proper developmental silencing in a mouse transacting BCL11A−/− environment. The findings herein indicate a model in which one (or more) trans-acting silencers of the embryonic globin genes, initially expressed throughout definitive erythropoiesis, have been altered during primate evolution, such that their expression is shifted to a later phase of definitive erythropoiesis, allowing for the evolution of a unique fetal hemoglobin expression stage. Here, it is shown that BCL11A represents one of the major factors regulating this switch. These findings allow for simplification of molecular models accounting for this critical developmental transition. This work provides not only unique insights into how alterations in gene expression occur in the course of evolution, but also reveals additional mechanistic clues to the clinically important fetal-to-adult hemoglobin switch in humans.

We claim:

1. A method for increasing fetal hemoglobin levels in a cell, the method comprising the steps of contacting a hematopoietic progenitor cell with an effective amount of a composition comprising an inhibitor of BCL11A, whereby fetal hemoglobin expression is increased in said cell, or its progeny, relative to said cell prior to said contacting.

2. The method of claim 1, wherein the hematopoietic progenitor cell is a cell of the erythroid lineage.

3. The method of claim 1, wherein the hematopoietic progenitor cell is contacted ex vivo or in vitro.

4. The method of claim 1, wherein the composition comprising an inhibitor of BCL11A inhibits BCL11A expression.

5. The method of claim 4, wherein the inhibitor of BCL11A expression is selected from a small molecule and a nucleic acid.

6. The method of claim 5, wherein the nucleic acid is a BCL11A specific RNA interference agent, or a vector encoding a BCL11A specific RNA interference agent.

7. The method of claim 6, wherein said RNA interference agent comprises one or more of the nucleotide sequences of SEQ ID NO: 1-6.

8. The method of claim 1, wherein the composition comprising an inhibitor of BCL11A inhibits BCL11A activity.

9. The method of claim 8, wherein the inhibitor of BCL11A activity is selected from the group consisting of an antibody against BCL11A or an antigen-binding fragment thereof, a small molecule, and a nucleic acid.

10. The method of claim 9, wherein the nucleic acid is a BCL11A specific RNA interference agent, a vector encoding a RNA interference agent, or an aptamer that binds BCL11A.

11. The method of claim 10, wherein said RNA interference agent comprises one or more of the nucleotide sequences of SEQ ID NO: 1-6.

12. A method for increasing fetal hemoglobin levels in a mammal in need thereof, the method comprising the step of contacting a hematopoietic progenitor cell in said mammal with an effective amount of a composition comprising an inhibitor of BCL11A, whereby fetal hemoglobin expression is increased in said mammal, relative to expression prior to said contacting.

13. The method of claim 12, wherein said mammal has been diagnosed with a hemoglobinopathy.

14. The method of claim 13, wherein said hemoglobinopathy is a β-hemoglobinopathy.

15. The method of claim 13, wherein the hemoglobinopathy is sickle cell disease.

16. The method of claim 13, wherein the hemoglobinopathy is β-thalassemia.

17. The method of claim 12, wherein the hematopoietic progenitor cell is contacted ex vivo or in vitro, and said cell or its progeny is administered to said mammal.

18. The method of claim 12, wherein said contacting comprises contacting said cell with a composition comprising of an inhibitor of BCL11A and a pharmaceutically acceptable carrier or diluent.

19. The method of claim 12, wherein the composition is administered by injection, infusion, instillation, or ingestion.

20. The method of claim 12, wherein the composition comprising an inhibitor of BCL11A inhibits BCL11A expression.

21. The method of claim 20, wherein the inhibitor of BCL11A expression is selected from a small molecule and a nucleic acid.

22. The method of claim 21, wherein the nucleic acid is a BCL11A specific RNA interference agent or a vector encoding a RNA interference agent, or an aptamer that binds BCL11A.

23. The method of claim 22, wherein said RNA interference agent comprises one or more of the nucleotide sequences of SEQ ID NO: 1-6.

24. The method of claim 12, wherein the composition comprising an inhibitor of BCL11A inhibits BCL11A activity.

25. The method of claim 24, wherein the inhibitor of BCL11A activity is selected from the group consisting of an antibody against BCL11A or an antigen-binding fragment thereof, a small molecule, and a nucleic acid.

26. The method of claim 25, wherein the nucleic acid is a BCL11A specific RNA interference agent, a vector encoding said RNA interference agent, or an aptamer that binds BCL11A.

27. The method of claim 26, wherein said RNA interference agent comprises one or more of the nucleotide sequences of SEQ ID NO: 1-6.

28. A method for identifying a modulator of BCL11A activity or expression, the method comprising contacting a hematopoietic progenitor cell with a composition comprising a test compound, and measuring the level of fetal hemoglobin or fetal hemoglobin mRNA in said cell or its progeny, wherein an increase in fetal hemoglobin is indicative that said test compound is a candidate inhibitor of BCL11A activity or expression.

29. The method of claim 28, wherein the hematopoietic progenitor cell is contacted in vivo, ex vivo, or in vitro.

30. The method of claim 28, wherein the cell is of human, non-human primate, or mammalian origin.

31. The method of claim 28, wherein the test compound is a small molecule, antibody or nucleic acid.

32. The method of claim 28, wherein the composition causes an increase in fetal hemoglobin mRNA or protein expression.

* * * * *

UNITED STATES PATENT AND TRADEMARK OFFICE
CERTIFICATE OF CORRECTION

PATENT NO. : 10,266,826 B2
APPLICATION NO. : 15/888350
DATED : April 23, 2019
INVENTOR(S) : Stuart H. Orkin and Vijay G. Sankaran It is certified that error appears in the above-identified patent and that said Letters Patent is hereby corrected as shown below:

In the Specification

At Column 1, Lines 26-29:
"This invention was made with Government Support under T32 GM07726, T32 GM07753-27, 5P01 HL32262-26, and 5R01 HL32259-27, all awarded by the National Institutes of Health. The Government has certain rights in the invention." should be replaced with -- This invention was made with government support under Grant Nos. HL032262 and HL032259, awarded by the National Institutes of Health. The Government has certain rights in the invention. --

Signed and Sealed this
Thirty-first Day of March, 2020

Andrei Iancu
*Director of the United States Patent and Trademark Office*

SEQUENCE LISTING

```
<160> NUMBER OF SEQ ID NOS: 28

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gagcacaaac ggaaacaau                                                  19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
gccacaggau gacgauugu                                                  19

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gcacuuaagc aaacgggaa                                                  19

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 4
acagaacacu cauggauua                                                19

<210> SEQ ID NO 5
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ccggcgcaca gaacactcat ggattctcga gaatccatga gtgttctgtg cgttttg      58

<210> SEQ ID NO 6
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccggccagag gatgacgatt gtttactcga gtaaacaatc gtcatcctct ggttttg      58

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gagaggcagc agcacatatc                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8 cagggtaaa caacgaggag                                                20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tggatgatct caagggcac                                                19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcagtggtat ctggaggaca                                              20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctgaggagaa gtctgccgtt a                                            21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agcatcagga gtggacagat                                              20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tggcctgtgg agtaaggtca a                                            21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gaagcagagg acaagttccc a                                            21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tggacaacct caaggagacc                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 16
acctctgggg tgaattcctt                                              20

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tttaacgatg gcctgaatca ctt                                          23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cagcacaatc acgatcatat tgc                                          23

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aaccccagca cttaagcaaa                                              20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acaggtgaga aggtcgtggt                                              20

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(21)
<223> OTHER INFORMATION: a, c, g, t, unknown or other

<400> SEQUENCE: 21
aannnnnnnn nnnnnnnnnn ntt                                          23

<210> SEQ ID NO 22
<211> LENGTH: 16
<212> TYPE: PRT
<213> ORGANISM: Mus sp.
```

```
<400> SEQUENCE: 22

Met Ser Arg Arg Lys Gln Gly Lys Pro Gln His Leu Ser Lys Arg Glu
1               5                   10                  15

<210> SEQ ID NO 23
<211> LENGTH: 16
<212> TYPE: PRT
<213> ORGANISM: Homo sapiens

<400> SEQUENCE: 23

Met Ser Arg Arg Lys Gln Gly Lys Pro Gln His Leu Ser Lys Arg Glu
1               5                   10                  15

<210> SEQ ID NO 24
<211> LENGTH: 16
<212> TYPE: PRT
<213> ORGANISM: Mus sp.

<400> SEQUENCE: 24

Met Ser Arg Arg Lys Gln Gly Asn Pro Gln His Leu Ser Gln Arg Glu
1               5                   10                  15

<210> SEQ ID NO 25
<211> LENGTH: 16
<212> TYPE: PRT
<213> ORGANISM: Mus sp.

<400> SEQUENCE: 25

Met Ser Arg Arg Lys Gln Ser Asn Pro Arg Gln Ile Lys Arg Ser Leu
1               5                   10                  15

<210> SEQ ID NO 26
<211> LENGTH: 16
<212> TYPE: PRT
<213> ORGANISM: Mus sp.

<400> SEQUENCE: 26

Met Ser Arg Arg Lys Gln Ala Lys Pro Arg Ser Leu Lys Asp Pro Asn
1               5                   10                  15

<210> SEQ ID NO 27
<211> LENGTH: 16
<212> TYPE: PRT
<213> ORGANISM: Mus sp.

<400> SEQUENCE: 27

Met Ser Arg Arg Lys Gln Ala Lys Pro Arg Ser Val Lys Val Glu Glu
1               5                   10                  15

<210> SEQ ID NO 28
<211> LENGTH: 16
<212> TYPE: PRT
<213> ORGANISM: Mus sp.

<400> SEQUENCE: 28

Met Ser Arg Arg Lys Gln Ala Lys Pro Gln His Phe Gln Ser Asp Pro
1               5                   10                  15
```